(12) United States Patent
Nishida et al.

(10) Patent No.: US 8,439,848 B2
(45) Date of Patent: May 14, 2013

(54) BLOOD TESTING DEVICE

(75) Inventors: Takeshi Nishida, Fukuoka (JP); Tetsuya Takashima, Ehime (JP)

(73) Assignee: Panasonic Corporation, Osaka (JP)

( * ) Notice: Subject to any disclaimer, the term of this patent is extended or adjusted under 35 U.S.C. 154(b) by 129 days.

(21) Appl. No.: 12/676,029

(22) PCT Filed: Sep. 4, 2008

(86) PCT No.: PCT/JP2008/002448
§ 371 (c)(1),
(2), (4) Date: Mar. 2, 2010

(87) PCT Pub. No.: WO2009/031312
PCT Pub. Date: Mar. 12, 2009

(65) Prior Publication Data
US 2010/0185119 A1 Jul. 22, 2010

(30) Foreign Application Priority Data
Sep. 4, 2007 (JP) ................................ 2007-228532

(51) Int. Cl.
*A61B 5/00* (2006.01)
*B65D 81/00* (2006.01)

(52) U.S. Cl.
USPC ........................................ 600/583; 600/584

(58) Field of Classification Search .................. 600/583, 600/347; 604/207; 436/169
See application file for complete search history.

(56) References Cited

U.S. PATENT DOCUMENTS

| | | | |
|---|---|---|---|
| 5,947,957 A | 9/1999 | Morris | |
| 5,993,439 A | 11/1999 | Costello et al. | |
| 7,374,545 B2 * | 5/2008 | Alroy | 600/583 |
| 7,378,007 B2 | 5/2008 | Moerman et al. | |
| 2006/0211127 A1 * | 9/2006 | Iwaki et al. | 436/169 |
| 2007/0142789 A1 * | 6/2007 | Fisher et al. | 604/207 |
| 2009/0043227 A1 | 2/2009 | Fujiwara et al. | |
| 2009/0177117 A1 | 7/2009 | Amano et al. | |
| 2009/0281455 A1 | 11/2009 | Fujiwara et al. | |
| 2009/0318834 A1 | 12/2009 | Fujiwara et al. | |
| 2010/0068795 A1 | 3/2010 | Shinohara et al. | |
| 2010/0168534 A1 * | 7/2010 | Matsumoto et al. | 600/309 |

FOREIGN PATENT DOCUMENTS

| | | |
|---|---|---|
| CA | 2646721 A1 * | 9/2007 |
| EP | 1627662 | 2/2006 |
| JP | 2001-309905 | 6/2001 |
| JP | 2003-524496 | 8/2003 |
| JP | 2003-265444 | 9/2003 |

* cited by examiner

*Primary Examiner* — Brian Szmal
*Assistant Examiner* — Fangemonique Smith
(74) *Attorney, Agent, or Firm* — Greenblum & Bernstein, P.L.C.

(57) ABSTRACT

A blood testing device that can perform blood testing having lighting intensity independent of the number of times of piercing. The blood testing device (21) has a cover unit (20) removably installed on negative pressure chambers (25a, 25b). The cover unit (20) has a circular tube section (20b) surrounding the optical axis of a laser unit (26) and having a predetermined length in the direction of the optical axis, a cover glass (20d) placed on the optical axis of the laser unit (26) so as to be located at that end of the circular tube section (20b) which is on the laser unit (26) side, and a slit (20e) for interconnecting the inside of the circular tube section (20b) and the negative pressure chamber (25a) outside the circular tube section (20b).

20 Claims, 17 Drawing Sheets

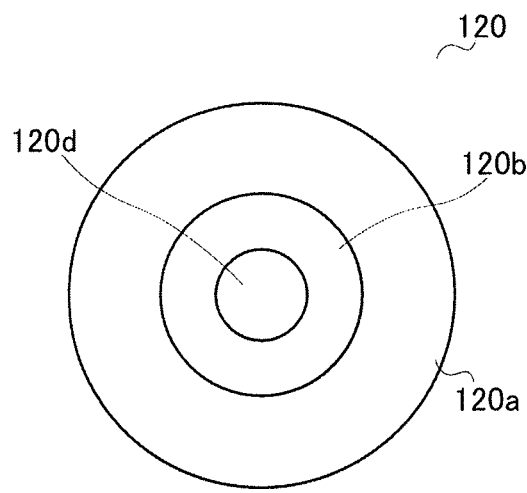
FIG.24A
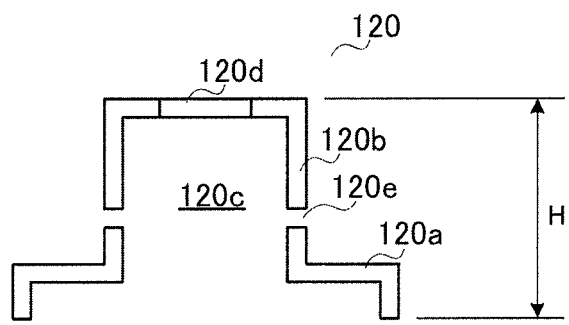
FIG.24B
| | FILM | GLASS |
|---|---|---|
| HEAT RESISTANCE | × | ○ |
| STRENGTH | × | ○ |
| COST | ○ | × |
FIG.25

PORTION THROUGH WHICH
LASER LIGHT PASSES

BLOOD TESTING DEVICE

TECHNICAL FIELD

The present invention relates to a blood test apparatus that punctures skin and so forth and tests blood.

BACKGROUND ART

Conventionally, the apparatuses disclosed in, for example, Patent Document 1, Patent Document 2 and Patent Document 3 have been known as blood test apparatuses. Now, the disclosed blood test apparatus in combination of Patent Document 1 and Patent Document 3 will be described.

FIG. 1 is a cross sectional view of an enlarged puncturing section of the blood test apparatus described in Patent Document 3, and here, negative pressure path 6 in communication with the negative pressure part and blood sensor 3 described in Patent Document 1 are added in the drawing.

In FIG. 1, the blood test apparatus includes puncturing section 4 that sandwiches blood sensor (hereinafter referred to as a sensor) 3, laser unit 5 that is provided to face puncturing section 4 and negative pressure chamber 4a that is provided in puncturing section 4, but a negative pressure means and a negative pressure button for applying a negative pressure to negative pressure chamber 4a and a puncturing button for operating the puncturing section are not shown in the drawing.

Now, the operation of the above-described blood test apparatus will be explained.

First, finger 9 touches puncturing section 4 as shown in FIG. 1. Then, the puncturing button is pressed. When the puncturing button is pressed, the negative pressure means operates and then a negative pressure is applied to inside negative pressure chamber 4a.

When a negative pressure is applied to negative pressure chamber 4a, skin 9a of finger 9 comes to swell. At the time skin 9a sufficiently swells, the puncturing button is pressed. When the puncturing button is pressed, laser light 5b is emitted from laser unit 5 and punctures skin 9a. When skin 9a is punctured, firstly evaporated materials 13 are scattered from skin 9a. After evaporated materials 13 are scattered, blood 10 exudes from the punctured skin 9a. The exuding blood 10 is taken in sensor 3. Then, after blood 10 reacts with a reagent placed in this sensor 3, a current value of the oxidation-reduction reaction is obtained by applying a voltage to the electrode in sensor 3, and then the current value is inputted to a measurement circuit section (not shown). This measurement circuit section calculates blood sugar levels and so forth based on the detected current value and displays the calculated blood sugar level on a display section (not shown).

Here, in order to adhere evaporated materials 13 on lens 5c provided on the optical axis of laser light from laser unit 5, film or cover glass 14 is attached on the top surface of negative pressure chamber 4a.

Patent Document 1: Japanese Patent Unexamined Publication No. 2001-309905;
Patent Document 2: Published Japanese Translation of PCT Application No. 2003-524496; and
Patent Document 3: U.S. Pat. No. 5,993,439

DISCLOSURE OF INVENTION

Problems to be Solved by the Invention

However, with such a conventional blood test apparatus, cover glass 14 is stained with scattered evaporated materials 13 every time the puncturing is performed. If cover glass 14 is stained, laser light 5b is attenuated, and therefore the expected puncturing depth cannot be obtained. Consequently, sufficient blood 10 required for measurement cannot be obtained. There has been a problem that a blood test cannot be performed accurately unless sufficient blood 10 is obtained. In addition, there has been a problem that it is necessary to replace cover glass 14 when the evaporated materials are adhered too much.

The present invention solves the above-described problems, and it is therefore an object of the present invention to provide a blood test apparatus that can test blood with a radiant intensity independent of the number of times puncturing is performed.

Means for Solving the Problem

The blood test apparatus according to the present invention has a configuration including: a housing; a laser emitting device that is provided in the housing and that punctures skin with laser light in a noncontact state; a blood sensor that analyzes blood exuding by puncturing; a holding section that holds the blood sensor; a negative pressure chamber that is provided in the holding section and through which the laser light from the laser emitting device penetrates; a negative pressure means that creates a negative pressure in a negative pressure space hermetically sealed between the skin and the negative pressure chamber; and a cover unit that is removably mounted to the negative pressure chamber. The cover unit includes: a cylindrical member that encloses an optical axis of laser light from the laser emitting device and has a predetermined length in a direction of the optical axis; a cover member that is disposed at the end of the cylindrical member in the laser emitting device side, on the optical axis of laser light from the laser emitting device; and a communication path that communicates an inside of the cylindrical member with the negative pressure chamber.

Advantageous Effects of Invention

According to the present invention, it is possible to easily replace appropriately a cover unit in which a cover member allowing laser light to pass through is mounted even if evaporated materials adhere on the cover member during the puncturing operation by removably mounting the cover unit in a negative pressure chamber. Consequently, the radiant intensity is not dependent on the number of times puncturing is performed, so that a planned amount of blood is obtained and therefore the blood test can be performed accurately.

In addition, since a communication path that communicates the inside of the cylindrical member with the negative pressure chamber is provided in the cover unit, a negative pressure can be applied to inside the cover unit.

BRIEF DESCRIPTION OF DRAWINGS

FIG. 24A is a plane view schematically showing the cover unit mounted to and removed from the sensor holding section of the blood test apparatus according to embodiment 8 of the present invention;

FIG. 24B is a cross sectional view of the cover unit mounted to and removed from the sensor holding section of the blood test apparatus according to embodiment 8;

FIG. 25 is a drawing explaining the materials of the cover glass of the blood test apparatus according to embodiment 8 using a table;

BEST MODE FOR CARRYING OUT THE INVENTION

Now, the embodiments of the present invention will be described in detail with reference to the drawings.

(Embodiment 1)

Figure 2:
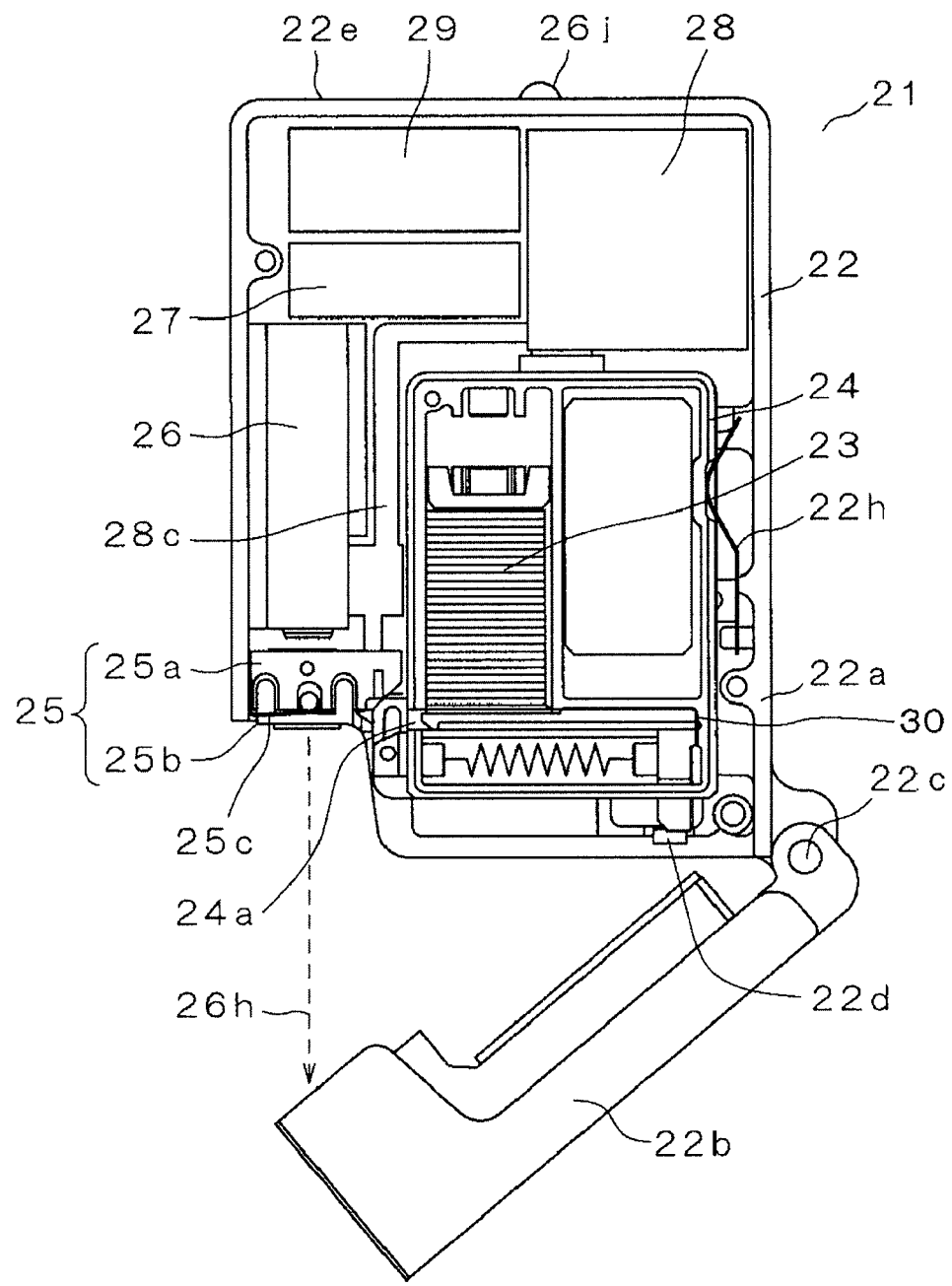
FIG. 2 is a perspective layout drawing of a blood test apparatus according to embodiment 1 of the present invention.

FIG. 2 is a perspective layout drawing of a blood test apparatus according to embodiment 1 of the present invention.

In FIG. 2, blood test apparatus 21 is formed of resin and has an approximately rectangular solid-shaped housing 22. This housing 22 is composed of main body 22a and cover 22b provided to rotate about supporting point 22c of main body 22a. The opening and closing of cover 22b is detected by opening and closing sensor 22d.

In main body 22a, blood sensors (hereinafter referred to as sensors) 23, cartridge 24, sensor outlet 24a, sensor holding section 25, laser unit 26, puncturing button 26j, measurement circuit section 27, negative pressure means 28, battery 29 and conveying means 30 that moves sensors 23 from cartridge 24.

Cartridge 24 stacks and stores sensors 23. In addition, sensor outlet 24a is provided in the lower part of cartridge 24.

[Sensor holding section 25 is coupled with sensor outlet 24a and is provided at the corner of one side of main body 22a. Sensor holding section 25 will be described in detail with reference to FIG. 3.

Laser unit 26 is formed to face sensor holding section 25.

Measurement circuit section 27 is provided between laser unit 26 and the other side 22e of main body 22a and is connected to laser unit 26.

Negative pressure means 28 applies a negative pressure to inside negative pressure chambers 28a and 28b (see FIG. 3) formed in sensor holding section 25 and to inside cartridge 24.

Battery 29 supplies electrical power to each component.

Conveying means 30 conveys sensor 23 stored in cartridge 24 at the bottom to sensor holding section 25.

FIG. 2 shows a state in which cover 22b is open. Cover 22b is provided to be able to rest at two-level opening angle with respect to main body 22a. The resting positions at the two-level opening angle include a first level resting position in which the cover rests at an opening angle about 30 degrees with respect to the main body and a second level resting position in which the cover rests at an opening angle about 90 degrees with respect to the main body.

Here, when cover 22b is opened, sensor outlet 24a opens and therefore sensor 23 in cartridge 24 at the bottom among sensors 23 is set between upper holder 25a and lower holder 25b by conveying means 30. Here, sensor 23 may not be necessarily set between upper holder 25a and lower holder 25b and may be set in a connector (not shown), which sandwiches an electrode section formed at the end of sensor 23.

By placing cover 22b in the first level resting position in which cover 22b opens about 30 degrees with respect to the main body, laser light 26h does not leak outside and therefore the safety can be assured. In addition, in order to replace cartridge 24, cover 22b is placed in the second-level resting position in which cover 22b is opened at about 90 degrees with respect to the main body, so that cartridge 24 can be easily inserted in and pulled out. In addition, while cover 22b is closed, laser light 26 is not emitted outside even if puncturing button 26j is pressed erroneously while blood test apparatus 21 is not used, so that the safety can be assured.

Figure 3:
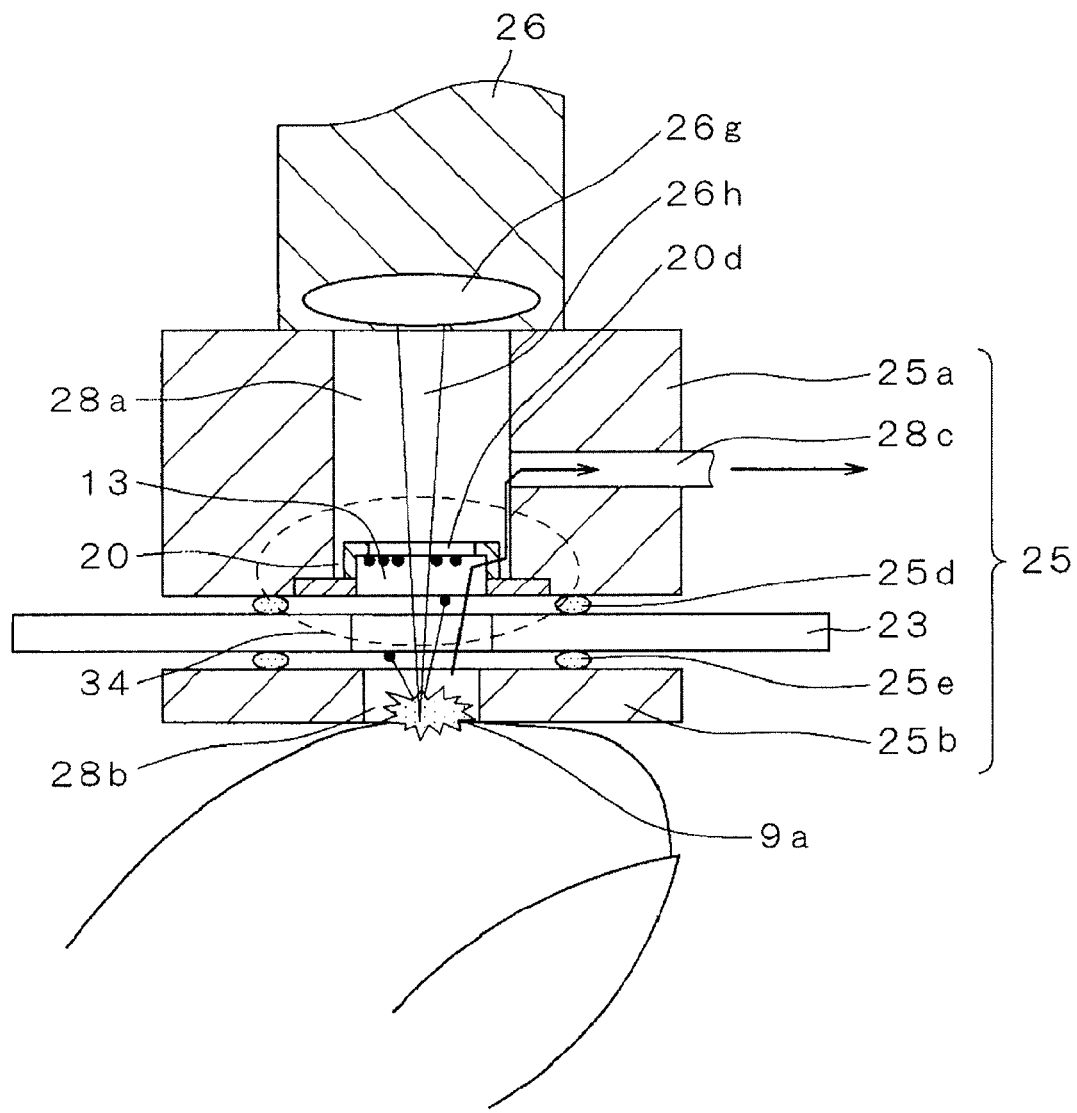
FIG. 3 is a cross sectional view of a sensor holding section and its neighborhood in the blood test apparatus according to embodiment 1.

FIG. 3 is a cross sectional view of the above-described sensor holding section 25 and its neighborhood.

In FIG. 3, sensor holding section 25 is composed of upper holder 25a and lower holder 25b and is provided on the same plane as on sensor outlet 24a to couple with sensor outlet 24a. Upper holder 25a is fixed to main body 22a and lower holder 25b is biased toward upper holder 25a by leaf spring 25c (see FIG. 2), and sensor 23 conveyed by conveying means 30 is inserted and sandwiched between upper holder 25a and lower holder 25b.

Upper holder 25a constituting sensor holding section 25 is firmly mounted at the tip (lens 26g side) of laser unit 26. Negative pressure chamber 28a through which laser light 26h penetrates is provided on upper holder 25a and negative pressure path 28c coupled with negative pressure means 28 is provided on the side wall surface of negative pressure chamber 28a, so that negative pressure path 28 connects negative pressure chamber 28a formed in upper holder 25a and negative pressure means 28.

Frame-like seal member 25d is attached to the lower part (a part facing lower holder 25) of upper holder 25a so as to enclose cover unit 20. In addition, seal member 25e is attached to upper part (a part facing upper holder 25a) of lower holder 25b facing seal member 25d. Sensor 23 is inserted between upper holder 25a to which seal member is attached and lower holder 25b to which seal member 25e is attached. Thus, seal members 25d and 25e can assure airtightness in the portion where laser light 26h passes through. A skin detecting sensor (not shown) is provided below lower holder 25b.

Negative pressure chamber 28b is provided in lower holder 25b. Negative pressure chamber 28b connects negative pressure chamber 28a and storing section 34 provided in sensor 23 in a straight line so as to allow laser light 26h to pass through.

Here, when lower holder 25b is hermetically sealed with skin 9a, the through-hole penetrating skin 9a, upper holder 25a and lower holder 25b constitute negative pressure spaces negative pressure chambers 28a and 28b.

In addition, cover unit 20 is removably mounted in the skin 9a side of negative pressure chamber 28a (hereinafter referred to as "the lower part of negative pressure chamber 28a", and in the downward direction in FIG. 3).

[Cover Unit 20]

Figure 4:
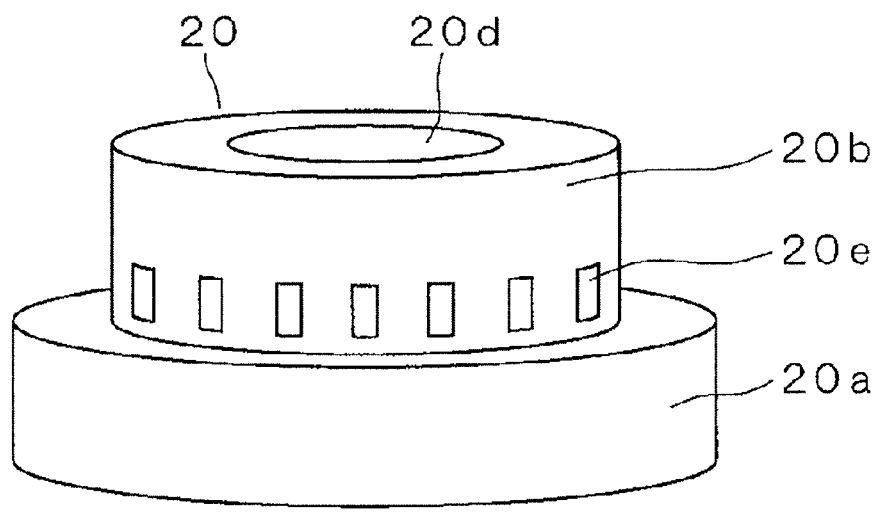
FIG. 4 is a perspective view of a cover unit mounted to and removed from the sensor holding section of the blood test apparatus according to embodiment 1.
Figure 5:
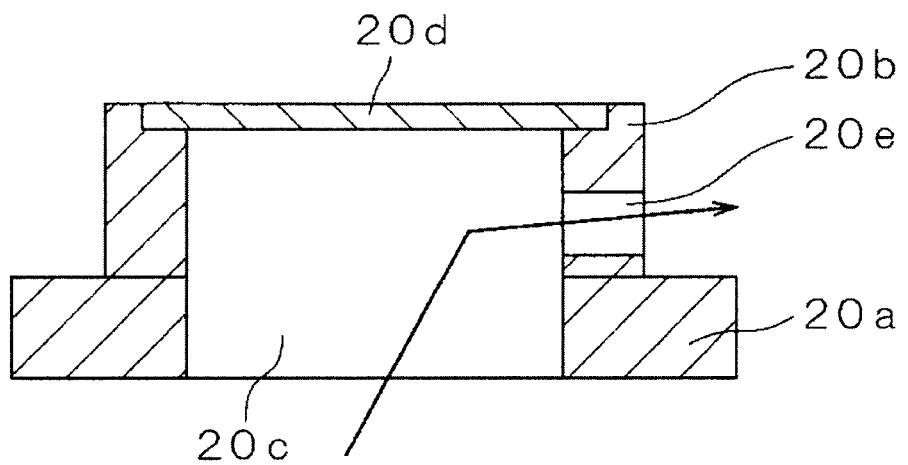
FIG. 5 is a cross sectional view of the cover unit mounted to and removed from the sensor holding section of the blood test apparatus according to embodiment 1.

FIG. 4 is a perspective view of cover unit 20 mounted to and removed from the above-described sensor holding section 25, and FIG. 5 is a cross sectional view of cover unit 20.

In FIG. 4 and FIG. 5, cover unit 20 has annular flange 20a forming the lower part of the flange structure and cylindrical member 20b surrounding the optical axis of laser light from laser unit 26. When being viewed from the side surface, cover unit 20 has a derby hat shape and includes cavity 20c inside. Cover glass 20d is mounted on the top surface of cylindrical member 20b. Cover glass 20d is made of glass (sapphire glass, fluorite and borosilicate glass) allowing light having the laser wavelength to pass through or plate glass having a thickness equal to or less than 0.3 mm, or fluororesin (e.g. PFA (Tetra Fluoro ethylene-perfluoro Alkylvinyl ether copolymer), PTFE (Poly Tetra Fluoro Ethylene) and FEP (Fluorinated Ethylene Propylene copolymer).

A plurality of slits 20e connecting cavity 20c with the outside is formed on cylindrical member 20b and communicate cavity 20c with negative pressure chamber 28a.

[Sensor 23]

Figure 6:
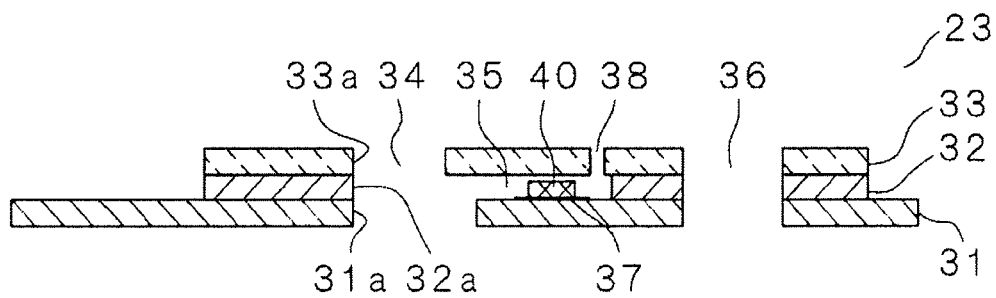
FIG. 6 is a cross sectional view of a sensor inserted in the sensor holding section of the blood test apparatus according to embodiment 1.
Figure 7:
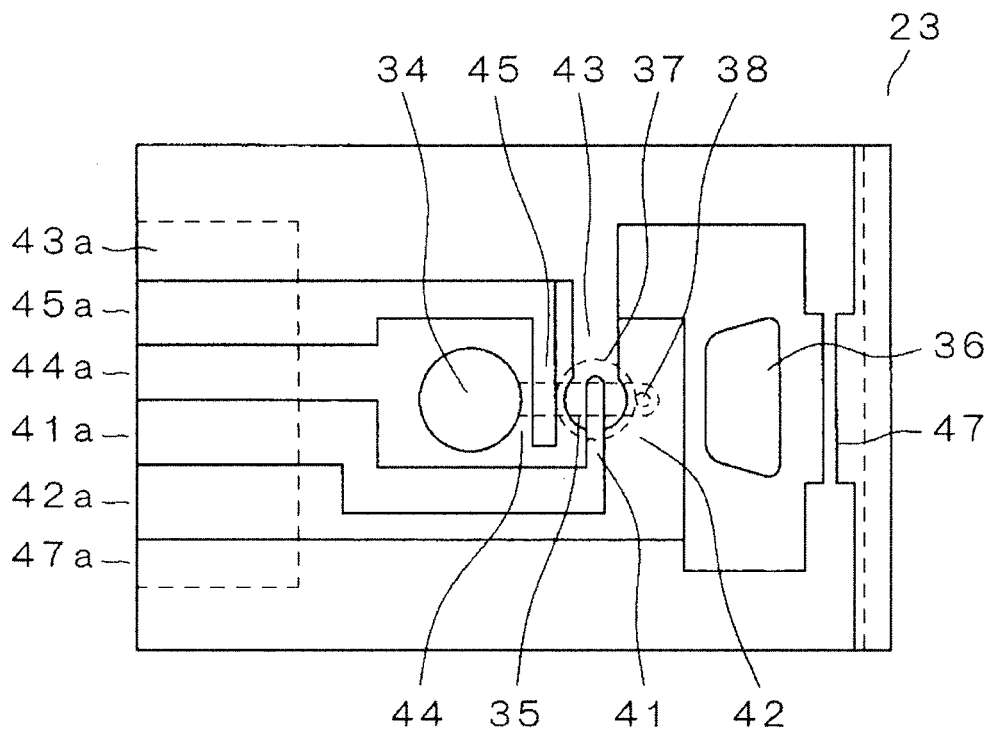
FIG. 7 is a perspective plane view of the sensor inserted in the sensor holding section of the blood test apparatus according to embodiment 1.
Figure 8:
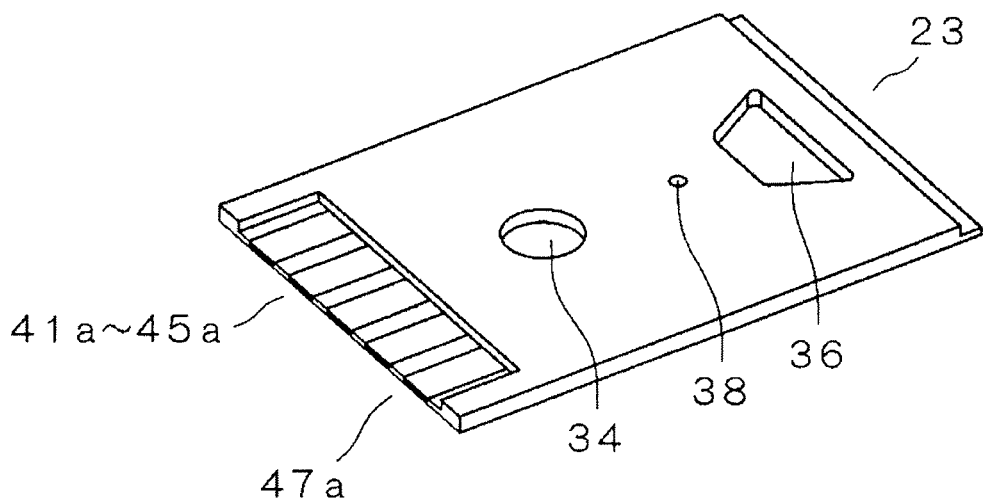
FIG. 8 is an external perspective view of the sensor inserted in the sensor holding section of the blood test apparatus according to embodiment 1.

FIG. 6 is a cross sectional view of sensor 23 inserted in the above-described sensor holding section 25, FIG. 7 is a perspective plane view of sensor 23 and FIG. 8 is an external perspective view of sensor 23.

In FIG. 6, sensor 23 is composed of substrate 31, spacer 32 pasted on the upper surface of substrate 31 and cover 33 pasted on the upper surface of spacer 32.

Storing section 34 for storing blood 10 is formed by connecting substrate hole 31a formed at approximately the center of substrate 31, spacer hole 32a formed in spacer 32 corresponding to substrate hole 31a and cover hole 33a formed in cover 33 corresponding to substrate hole 31a to communicate with each other. In addition, positioning hole 36 serves to determine the position in which sensor 23 is mounted in holding section 25 and is provided to penetrate sensor 23.

Supply path 35 for supplying blood 10 is coupled with one end of storing section 34. Supply path 35 introduces blood 10 stored in storing section 34 to detecting section 37 at a breath by capillary action. In addition, the other end of supply path 35 is coupled with air hole 38. The capacity of storing section 34 is 0.904 μL and the capacity of supply path 35 is 0.144 μL. As described above, the test can be performed using a small amount of blood and therefore the burden of the patient is reduced.

Reagent 40 is placed on detecting section 37. Reagent 40 can be obtained by adding and dissolving PQQ-GDH (0.1 to 5.0 U/sensor), potassium ferricyanide (10 to 200 millimole), maltitol (1 to 50 millimole) and taurine (20 to 200 millimole) in a CMC solution of 0.01 to 2.0 wt % to prepare a reagent solution, by dropping the reagent solution on detection electrodes 41 and 43 (see FIG. 7) formed on substrate 161 and drying. When this reagent 40 absorbs moisture, the performance of reagent 40 deteriorates progressively.

Here, an electrically conductive layer is formed on the upper surface of substrate 31 by the sputtering method or the vapor deposition method using materials such as gold, platinum, or palladium. Detection electrodes 41 to 45 (see FIG. 10), connection electrodes 41a to 45a derived from these detection electrodes 41 to 45 and an identification electrode 47a are integrally formed by applying laser machining to the electrically conductive layer.

In addition, the same material, polyethylene terephthalate (PET), is used for substrate 31, spacer 32 and cover 33. By using the same material, the management cost can be reduced.

In FIG. 7, connection electrodes 41a to 45a and identification electrode 47a are formed at one end of sensor 23. Identification electrode 47, which has a conductor pattern shown in FIG. 7, is formed between connection electrode 43a and identification electrode 47a.

Storing section 34 for storing blood 10 is provided at approximately the center of sensor 23, and supply path 35 of which one end is connected to this storing section 34 is provided toward detection electrode 42. Then, the other end of supply path 35 is coupled with air hole 38. Storing section 34, detection electrode 44 connected to connection electrode 44a, detection electrode 45 connected to connection electrode 45a, again detection electrode 44 connected to connection electrode 44a, detection electrode 43 connected to connection electrode 43a, detection electrode 41 connected to connection electrode 41a, again detection electrode 43 connected to connection electrode 43a and detection electrode 42 connected to connection electrode 42a, are provided on supply path 35, in the order described. In addition, reagent 40 (see FIG. 6) is placed on detection electrodes 41 and 43.

Whether sensor 23 is mounted in sensor holding section can be identified based on whether there is electrical conduction between connection electrode 43a and identification electrode 47a. That is, when this sensor 23 is conveyed to sensor holding section 25, the electrical conduction between connection electrode 43a and identification electrode 47a is detected, so that whether sensor 23 is mounted correctly in sensor holding section 25 can be detected. If there is no electrical conduction, sensor 23 is not mounted in sensor holding section 25 can be detected. In this case, a warning indication can be displayed on display section 55 (see FIG. 11) of blood test apparatus 21.

In addition, it is possible to store information of the calibration curve to be used and also manufacturing information by changing the electrical resistance of identifying section 47. A blood test can be performed more accurately by using those information.

As shown in FIG. 8, sensor 23 is formed by a rectangular plate. Storing section 34 is formed at approximately the center of this plate, and connection electrodes 41a to 45a and identification electrode 47a are formed at one end of the plate. In addition, positioning hole 36 is formed near the other end of the plate. This positioning hole 36 has a trapezoidal shape narrowing toward the storing section 34 side. Air hole 38 is formed between this positioning hole 36 and storing section 34.

[Cartridge 24]

Figure 9:
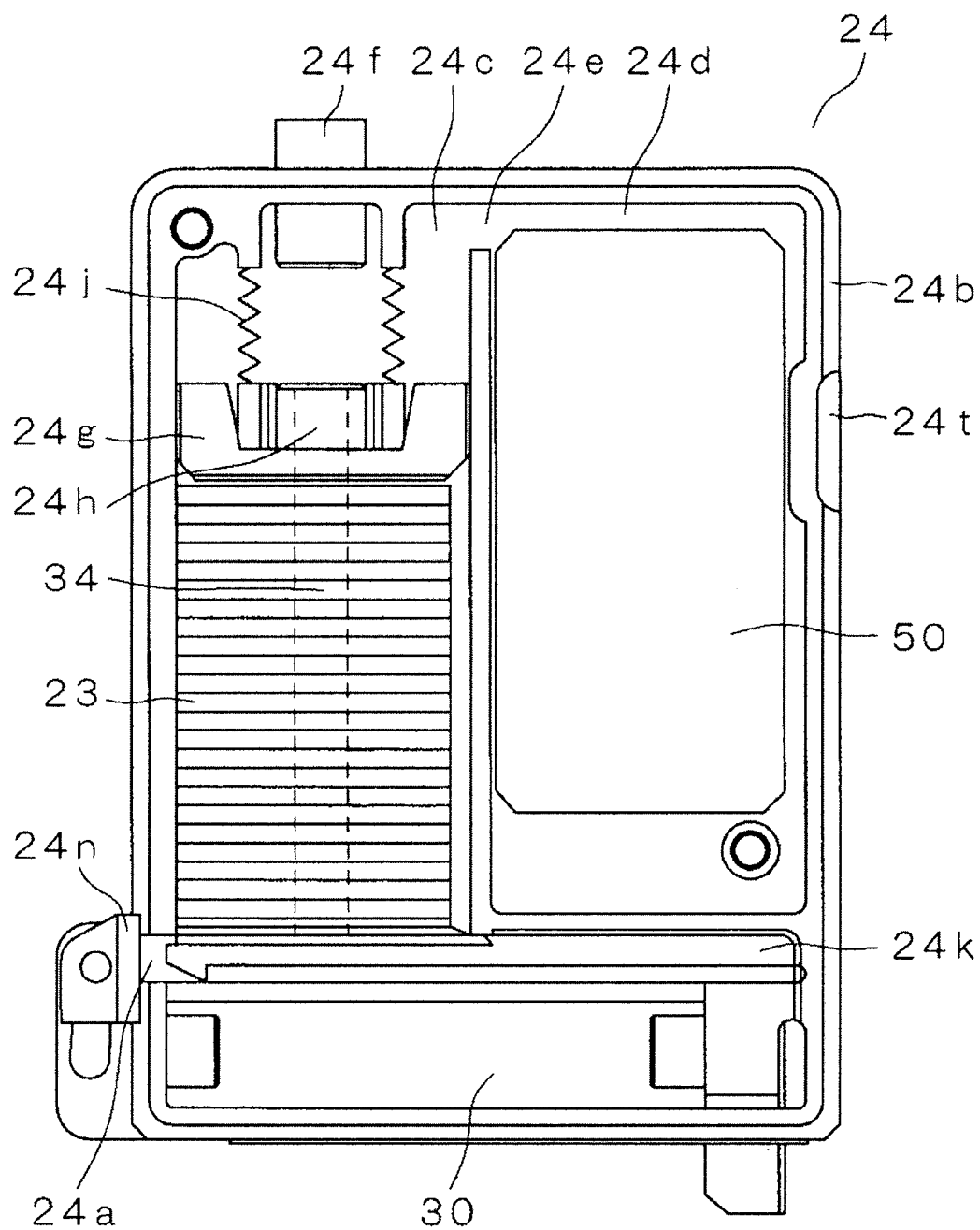
FIG. 9 is a perspective layout drawing of a cartridge that stacks and stores sensors of the blood test apparatus according to embodiment 1.

FIG. 9 is a perspective layout drawing of cartridge 24 that stacks and stores the above-described sensors 23.

In FIG. 9, cartridge 24 has case 24b made of resin. Sensor chamber 24c is provided in case 24b, and sensors 23 are stacked and stored in sensor chamber 24c. Drying chamber 24d is provided parallel to sensor chamber 24c and communicates with sensor chamber 24c through passage 24e. The capacity for containing drying air is increased by providing drying chamber 24d, so that it is possible to prevent sensor 23 from deteriorating for a long time without being influenced by dampness. Moreover, this effect is more improved by storing desiccant 50 in this drying chamber 24.

Negative pressure path 24f is formed above negative pressure chamber 24c and a negative pressure is supplied from negative pressure means 28 through this negative pressure path 24f. By this means, the inside of sensor chamber 24c is protected from the dampness. Pressure plate 24g presses down stacked and stored sensors 23. Hole 24h is formed at approximately the center of pressure plate 24g. Hole 24h corresponds to storing section 34 (see FIG. 6 to FIG. 8) formed in sensor 23. Accordingly, the negative pressure introduced from negative pressure path 24f dries the inside of storing section 34 of each sensor 23 through hole 24 and protects reagent 40 (see FIG. 6) provided to communicate with storing section 34 from deteriorating.

In addition, when desiccant 50 is stored in drying chamber 24d, the dry air supplied from drying chamber 24d also dries the inside of storing section 34 of each sensor 23 through passage 24e and therefore protects reagent 40 from deteriorating. In this case, since a negative pressure is supplied through negative pressure path 24f, large desiccant 50 may be unnecessary. Pressure plate 24g is biased downward by spring 24j.

Slider plate 24k is provided to slidably move below sensor chamber 24c. Slider plate 24k conveys sensor 23 at the bottom outside sensor outlet 24a. Conveying means 30 can move slider plate 24k.

Sensor outlet 24a is opened and closed by movable shutter 24n. Then, shutter 24n is opened and closed in conjunction with open and close of cover 22b. That is, open of cover 22b allows shutter 24n to "open", and close of cover 22b allows shutter 24n to "close". When shutter 24n "closes", the inside of case 24b hermetically sealed and therefore reagent 40 in sensor 23 is protected from dampness.

Positioning concave part 24t is provided on the side surface of case 24b, and positioning convex part 22h (see FIG. 2) formed by a leaf spring is provided in main body 22a. Positioning is performed by fitting positioning convex part 22h in positioning concave part 24t.

[Laser Unit 26]

Figure 10:
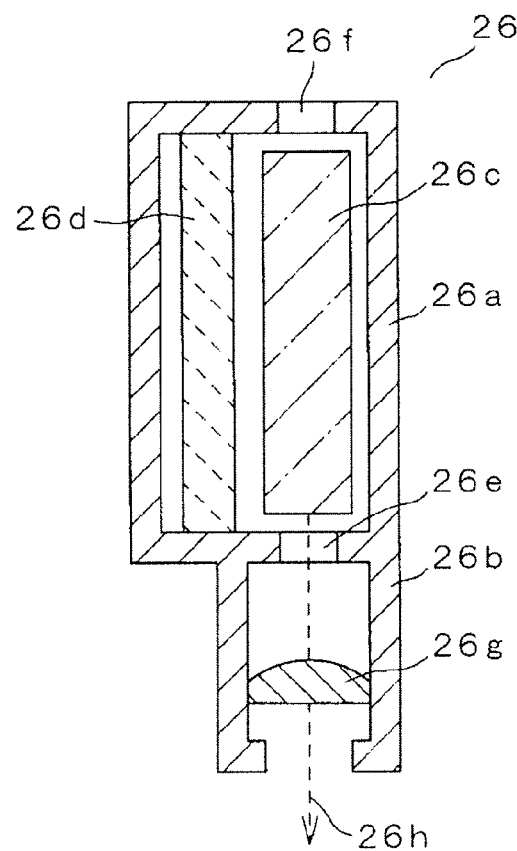
FIG. 10 is a cross sectional view of a laser unit of the blood test apparatus according to embodiment 1.

FIG. 10 is a cross sectional view of the above-described laser unit 26.

In FIG. 10, laser unit 26 is composed of oscillating tube 26a and cylindrical body 26b coupled to this oscillating tube 26a. Er:YAG (yttrium, aluminum, garnet) laser rod 26c and flash light source 26d (an example of light source) are housed in oscillating tube 26a. Partially transmitting mirror 26e having a reflectivity of about 85% to 95% is mounted at one end of oscillating tube 26a, and approximately total reflecting mirror 26f having a reflectivity equal to or more than 99.5% is mounted at the other end of oscillating tube 26a. Convex lens 26g is mounted in cylindrical body 26b beyond partially transmitting mirror 26e and is set to focus laser light 26h near the skin of the patient.

The operation of laser unit 26 having the configuration described above will be explained in detail.

Puncturing button 26j (see FIG. 2 and FIG. 11) is pressed. After puncturing button 26j is pressed to apply a voltage of about 200 V to 700 V to both ends of flash light source 26d, the voltage of about 5 to 10 kV is applied instantaneously to the both ends of flash light source 26d as a trigger voltage. As a result of this, the pressure of the spark coil is raised and xenon gas sealed in the flash lamp is ionized, and therefore a current flows and the xenon gas is discharged and then light is emitted. This light is excitation light. This excitation light emitted from flash light source 26d enters laser rod 26c and excites a laser activating material (erbium (Er)) doped in the material of the laser rod to generate light. This phenomenon is stimulated emission. The generated light resonates among total reflection mirror 26f, laser rod 26c and partially transmitting mirror 26 and is amplified. Part of this amplified laser light passes through partially transmitting mirror 26e. This laser light 26h passing through partially transmitting mirror 26e is emitted through focusing lens 26g and focuses on near skin 9a. The appropriate focal depth for puncturing is plus or minus 0.1 mm to 1.5 mm to or from the surface of skin 9a. In the present embodiment, the puncturing depth is minus 0.5 mm from skin 9a.

The present embodiment employs laser unit 26 that can puncture skin 9a of the patient in a noncontact state, so that it is sanitary. In addition, laser unit 26 has no moving components, which are used for puncturing with a needle, so that occurrences of failure are reduced. Here, this laser light 26h punctures skin with a voltage about 200 V to 500 V. Therefore, the patient feels little pain.

[Negative Pressure Means 28]

Next, negative pressure means 28 will be described. A negative pressure provided by negative pressure means 28 such as an air pump (not shown) is supplied to negative pressure path 24f (see FIG. 9) provided in cartridge 24 and negative pressure chambers 28a and 28b (see FIG. 2) formed in upper and lower holders 25a and 25b, respectively. The negative pressure supplied to negative pressure path 24f and negative pressure chambers 28a and 28b is switched by a valve. Therefore, the negative pressure can be supplied to negative pressure path 24f and negative pressure chambers 28a and 28b, respectively by one negative pressure means 28.

[Measurement Circuit Section 27]

Figure 11:
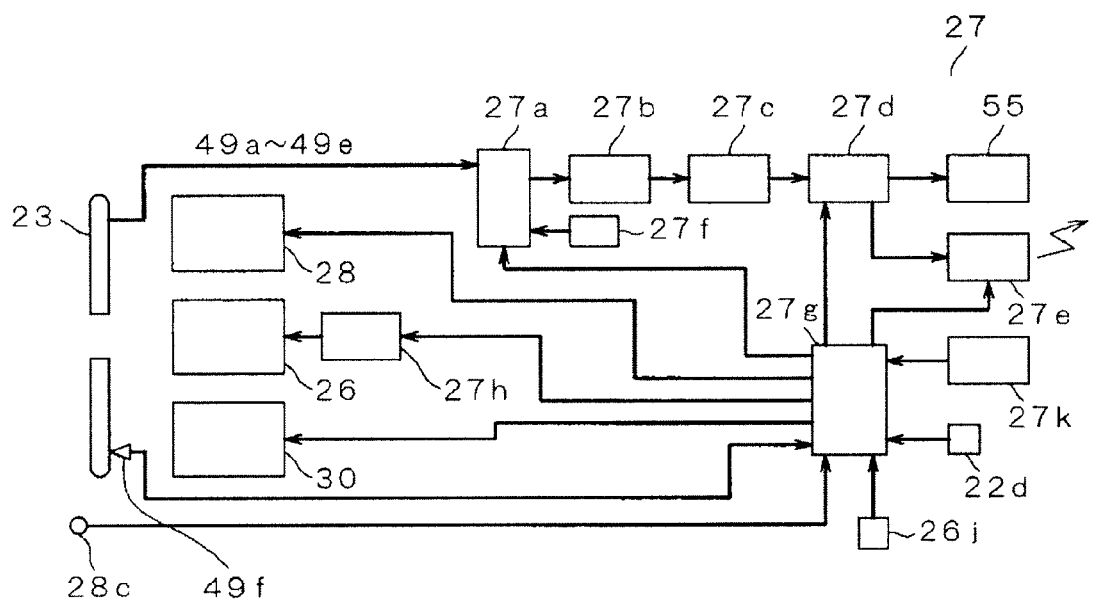
FIG. 11 is a block diagram showing a configuration of a measurement circuit section and its neighborhood in the blood test apparatus according to embodiment 1.

FIG. 11 is a block diagram showing a configuration of the above-described measurement circuit 27 and its neighborhood.

In FIG. 11, connection electrodes 41a to 45a (see FIG. 7) are connected with switching circuit 27a through connectors 49a to 49e. The output of this switching circuit 27a is connected to the input of current/voltage convertor 27b. The output of this current/voltage convertor 27b is inputted to computing section 27d through analog/digital convertor (hereinafter referred to as an A/D convertor). The output of computing section 27d is inputted to display section 55 made of liquid crystal and communicating section 27e. In addition, reference voltage source 27f is connected to switching circuit 27a. Here, this reference voltage source 27f may be a ground potential.

Control section 27g controls the entire operation of the test apparatus according to the present invention. The output of this control section 27g is inputted to high voltage generating circuit 27h connected to laser unit 26, a control terminal of switching circuit 27a, computing section 27d, communicating section 27e, negative pressure means 28 and conveying means 30. In addition, opening and closing sensor 22d, puncturing button 26j, skin detecting sensor 28c, timer 27k and connector 49f are connected to the input of control section 27g.

Next, operation of measurement circuit section 27 will be described.

First, puncturing button 26j is pressed to puncture skin 9a by laser unit 26. Then, the property of blood 10 exuding by puncturing is measured. In the measurement operation, switching circuit 27a is switched to connect detection electrode 41 (see FIG. 7) to current/voltage convertor 27b. In addition, detection electrode 42 serving as a detecting electrode for detecting an inflow of blood 10 is connected to reference voltage source 27f. Then, a constant voltage is applied between detection electrode 41 and detection electrode 42. In this state, a current flows between detection electrodes 41 and 42 if blood 10 flows in. This current is converted into a voltage by current/voltage convertor 27b, and the voltage value is converted into a digital value by A/D convertor 27c. Then, the digital value is outputted to computing section 27d. Computing section 27d detects blood 10 has sufficiently flowed in based on the digital value. Here, at this time, the operation of negative pressure means 28 is turned off.

Next, glucose, which is a component of blood, will be measured. To measure the glucose level, first, switching circuit 27a is switched by a command from control section 27g, and detection electrode 41 serving as a working electrode for measuring the glucose level is connected to current/voltage convertor 27b. In addition, detection electrode 43 serving as a counter electrode for measuring the glucose level is connected to reference voltage source 27f.

Here, for example, while the glucose in blood and its oxidation-reduction enzyme react for a given period of time, current/voltage convertor 27b and reference voltage source 27f are turned off. Then, after a certain period of time (1 to 10 seconds) has passed, a certain voltage (0.2 to 0.5 V) is applied between detection electrodes 41 and 43 by a command from control section 27g. By this means, a current flows between detection electrodes 41 and 43. This current is converted into a voltage by current/voltage convertor 27b, and the voltage value is converted into a digital value by A/D convertor 27c. Then, this digital value is outputted to computing section 27d. Computing section 27d converts this digital value to a glucose level.

Although an example of glucose measurement has been described above, the blood test apparatus is applicable to measurement of blood components other than glucose such as lactate acid or cholesterol levels by changing reagent 40 of sensor 23.

Now, the operation of blood test apparatus 21 configured as described above will be explained.

First, the overall operation of blood test apparatus 21 will be described.

When puncturing button 26j is pressed by touching skin 9 on lower holder 25b of blood test apparatus 21, laser light 26h is emitted from laser unit 26.

The emitted laser light 26h passes straight through negative pressure chamber 28a, cover unit 20, storing section 34 (see FIG. 6) of sensor 23 and negative pressure chamber 28b, and punctures skin 9a. When skin 9a is punctured, firstly evaporated materials 13 scatter. These evaporated materials 13 adhere on cover glass 20d constituting cover unit 20. After evaporated materials 13 scatter, blood 10 exudes. Blood 10 is stored in storing section 34. Blood 10 is taken in detecting section 37 (see FIG. 7) and reacts with reagent 40. After that, when a voltage is applied to the electrode in sensor 23, oxidation-reduction reaction occurs and the resulting signal is measured by measurement circuit 27.

Next a test method using blood test apparatus 21 will be described.

Figure 12:
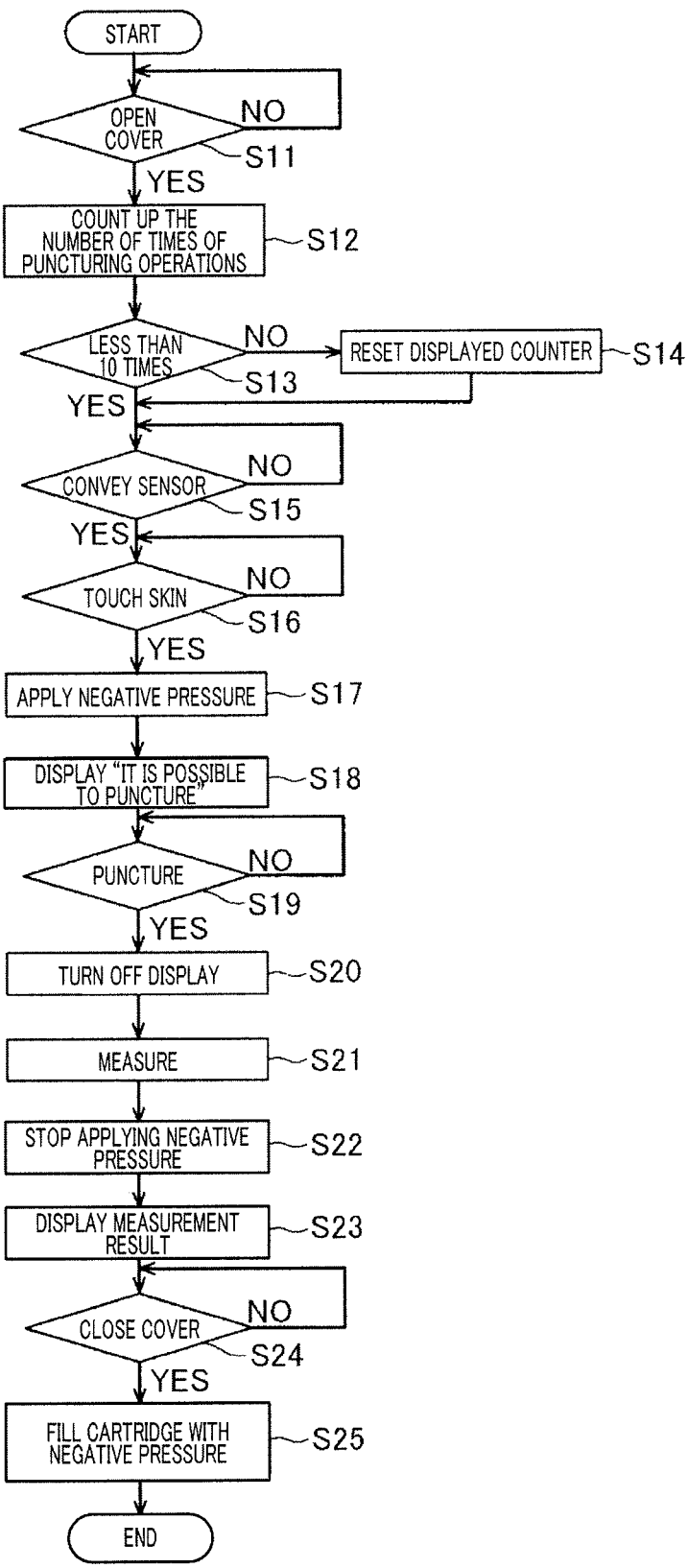
FIG. 12 is a flowchart showing a test method using the blood test apparatus according to embodiment 1.

FIG. 12 is a flowchart showing a test method using blood test apparatus 21. Control section 27g is configured by a microprocessor and so forth, and the flow is repeatedly performed by this microprocessor at a predetermined timing.

First, in step S11, cover 22b is opened. Opening and closing sensor 22d detects the open state of cover 22b of blood test apparatus 21. The detection signal from opening and closing sensor 22d is inputted to control section 27g, and then control section 27g receives this detection signal and turns on the power supply of laser unit 26. If the opening state of cover 22 of blood test apparatus 21 is not detected, control section 27g waits in this state.

In step S12, control section 27g counts up the number of times puncturing is performed with a puncturing counter after cover unit 20 is newly mounted. This puncturing counter is reset when cover unit 20 is newly mounted.

In step S13, control section 27g determines whether the number of times puncturing is performed by the puncturing counter is equal to or less than a predetermined number of times (10 times).

When the number of times puncturing is performed by the puncturing counter is more than 10 times, control section 27g displays a message indicating to replace cover unit 20 in step S14. Then, after control section 27g checks the replacement of glass cover unit 20 by an electrical signal and resets the puncturing counter, and the step moves to step S15. When the number of times puncturing is performed by the puncturing counter is equal to or less than 10 times, the step moves directly to step S15.

In step S15, control section 27g activates conveying means 30 and determines whether sensor 23 is conveyed to a predetermined position. That is, slider plate 24k is moved toward sensor outlet 24a, so that sensor 23, at the bottom among stacked and stored sensors 23, is conveyed to sensor holding section 25. This conveyance is checked by detecting electrical conduction between connection electrode 43a and identification electrode 47a of sensor 23. After that, slider plate 24k returns to a standby state by conveying means 30.

When the conveyance of the sensor is completed, control section 27g displays to prompt holding section 25 to contact skin 9 on display section 55 (see FIG. 11) in step S16. The patient follows the indication by display section 55 and touches blood test apparatus 21 with his/her skin 9a. This touch with skin 9a is detected by skin detecting sensor 28c.

When checking the touch with skin 9a, control section 27g operates negative pressure means 28 to create a negative pressure in negative pressure chambers 28a and 28b provided in sensor holding section 25. Skin 9a swells by applying a negative pressure. In addition, at the time the output of skin detecting sensor 28c is detected, high voltage generating circuit 27h may be operated to start charging a capacitor with a high voltage.

In step S18, control section 27g displays an indication that it is possible to perform a puncturing operation on display section 55. That is, when the current changes as a result of the operation of negative pressure means 28 and the charging with a high voltage is completed by high voltage generating circuit 27h, or when timer 27k measures the passage of a predetermined time period, control section 27g judges that the charging with the high voltage is enough to perform a puncturing operation and that skin 9a sufficiently swells in storing section 34, and displays the indication that it is possible to perform a puncturing operation on display section 55.

In step S19, control section 27g waits until puncturing button 26j is pressed. Here, this operation to press puncturing button 26j in step S19 may be performed automatically.

When puncturing button 26j is pressed, control section 27g turns off the indication that it is possible to perform a puncturing operation in step S20.

In step S21, control section 27g performs the measurement. The measurement is performed as follows. When skin 9a is punctured, exuding blood 10 is taken in storing section 34. This blood 10 taken into storing section 34 is introduced into detecting section 37 at a breath and at a constant flow rate by capillary action of supply path 35 and the blood sugar level of blood 10 is measured.

In step S22, control section 27g stops the operation of negative pressure means 28. Here, at the time this measurement of the blood sugar level is completed, or at the rime blood 10 reaches detection electrode 42, negative pressure means 28 may be turned off.

In step S23, the measurement result of the blood sugar level is displayed on display section 55. Here, this measurement result of the blood sugar level may be transmitted from communicating section 27e automatically to another device such as an injection device.

In step S24, opening and closing sensor 22d detects the closed state of cover 22b of blood test apparatus 21. The operation of shutter 24n of cartridge 24 is in conjunction with the closing operation of cover 22b, so that sensor outlet 24a is closed. Opening and closing sensor 22d detects the closed state of cover 22b and reports this fact to control section 27g, and then the step moves to step S25.

In step S25, control section 27g creates a negative pressure in cartridge 24 for a predetermined time period and ends this flow. Here, the reason to place the inside of cartridge 24 in the negative pressure state is that blood sensor 23 is prevented from deteriorating by the dampness by eliminating dampness in cartridge 24.

Specifically, after operating negative pressure means 28 for a predetermined time period to create a negative pressure in cartridge 24, control section 27g stops creating a negative pressure and turns off the power supply of blood test apparatus 21 to end this flow.

As described above, in step S13, the indication that it is necessary or unnecessary to replace cover unit 20 is displayed on display section 55, based on the number of times puncturing is performed after cover unit 20 is replaced. Reliable data can be easily obtained by performing the operation following this indication.

Moreover, sensor outlet 24a is opened in conjunction with open of cover 22b in step S11, and sensor outlet 24a is closed in conjunction with close of cover 22b in step S24. It is not necessary to perform an extra operation in order to open and close sensor outlet 24a and therefore the burden is removed.

In addition, after sensor 23 is conveyed in step S15, a puncturing operation is performed in step S19. Since this puncturing operation is performed to penetrate (see FIG. 2) storing section 34, exuding blood 10 is all stored in storing section 34 and is used for the blood test. Exuding blood 10 is efficiently used and the burden on the patient is minimized.

As described above, blood test apparatus 21 is provided in housing 22 and has: laser unit 26 that punctures skin with laser light in a noncontact state; sensor holding section 25 that holds sensor 23; negative pressure chambers 28a and 28b in sensor holding section 25, where laser light penetrates through; negative pressure means 28 that applies a negative pressure to a portion hermetically sealed by skin 9a and negative pressure chamber 28b; and cover unit 20 that is removably mounted in negative pressure chamber 28a. In addition, cover unit 20 encloses the optical axis of laser light from laser unit 26 and has: cylindrical member 20b having a predetermined length in the direction of this optical axis; cover glass 20d disposed at the end of cylindrical member 20b in the laser unit 26 side and located on the optical axis of laser light from laser unit 26; and slits 20e that communicate the inside of cylindrical member 20b with negative pressure chamber 28a. By this means, even if evaporated materials 13 adhere on cover glass 20d, cover unit 20 on which this cover glass 20d is mounted can be easily replaced appropriately. Therefore, the radiant intensity independent of the number of times puncturing is performed is provided, so that a planned amount of blood can be obtained and therefore the blood test can be performed accurately.

In addition, since slits 20e that communicate with negative pressure chamber 28a are provided in the over unit, a negative pressure can be applied to inside cover unit 20.

Here, cover glass 20d disposed at the end of cylindrical member 20b in the laser unit 26 side is located on the optical axis of laser light from laser unit 26. This means a case in which cover glass 20d is located at a certain angle with respect to the optical axis of laser light from laser unit 26, and preferably cover glass 20d is orthogonal to the optical axis.

(Embodiment 2)

Figure 13:
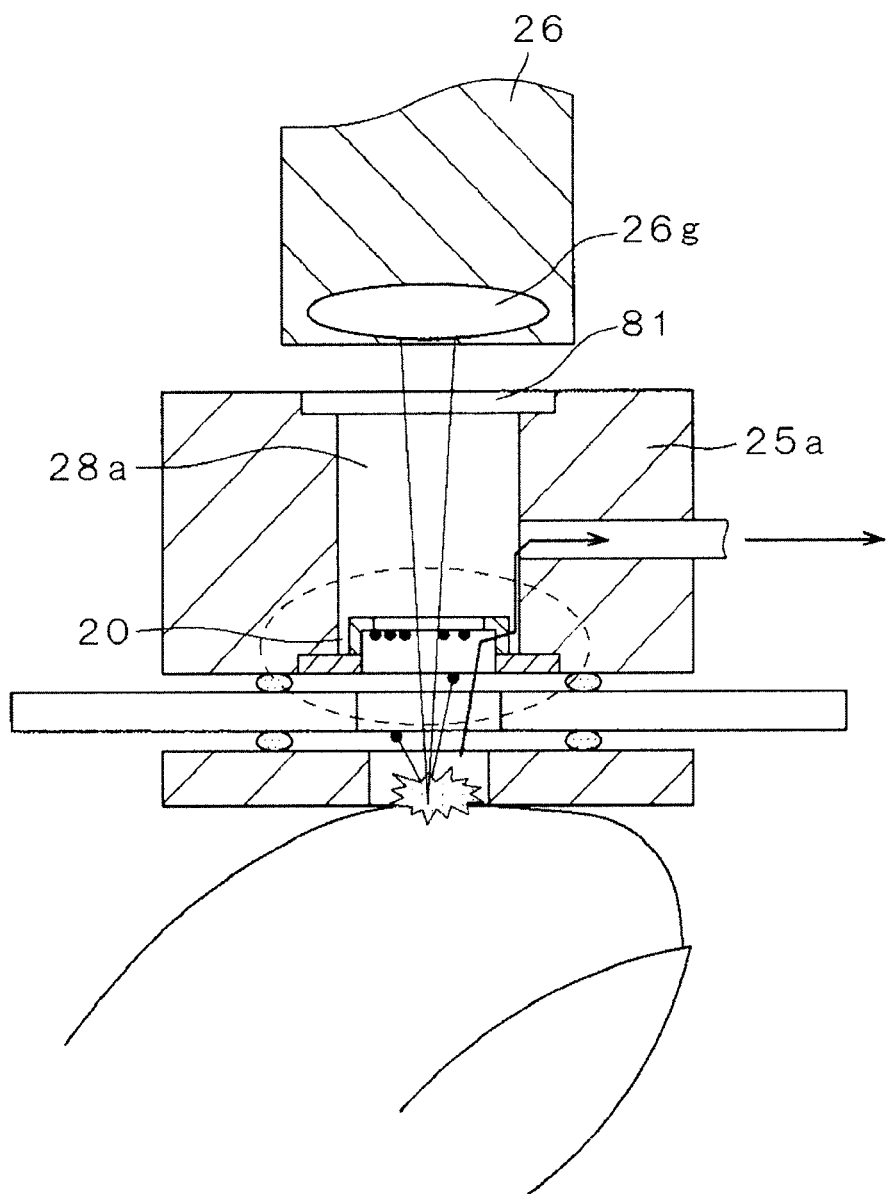
FIG. 13 is a cross sectional view of the sensor holding section and its neighborhood in the blood test apparatus according to embodiment 2 of the present invention.

FIG. 13 is a cross sectional view of sensor holding section 25 and its neighborhood in the blood test apparatus according to embodiment 2 of the present invention. The same components as in FIG. 3 will be assigned the same reference numerals and overlapping descriptions will be omitted.

As shown in FIG. 13, negative pressure chamber 28a is hermetically sealed by providing glass 81 allowing light to pass through in the upper part of upper holder 25a. By this configuration, even if part of evaporated materials 13 passes through slits 20e (see FIG. 4), these evaporated materials 13 adhere on glass 81, so that lens 26g of laser unit 26 is not stained with those evaporated materials 13. Therefore, blood 10 can be measured accurately.

(Embodiment 3)

Figure 14:
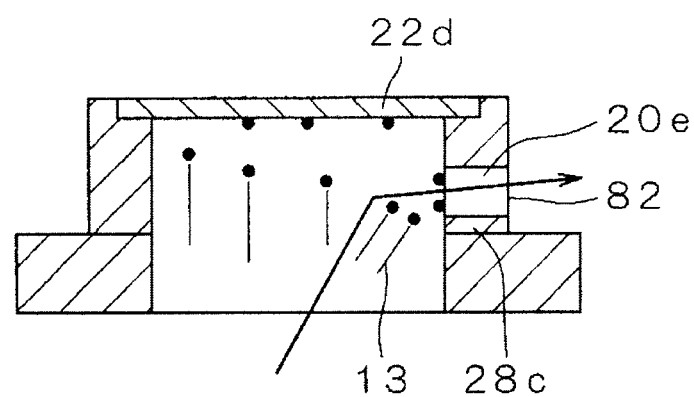
FIG. 14 is a cross sectional view of a cover unit mounted to and removed from the sensor holding section of the blood test apparatus according to embodiment 3 of the present invention.

FIG. 14 is a cross sectional view of a cover unit removably mounted to sensor holding section 25 of the blood test apparatus according to embodiment 3 of the present invention. The same components as in FIG. 5 will be assigned the same reference numerals and overlapping descriptions will be omitted.

As shown in FIG. 14, filter 82 is attached to slit 20e formed in the cover unit. Membrane filter 82 and so forth, which allow the air to pass through but do not allow solid to pass through, are suitable for filter 82. Evaporated materials 13 are prevented from flowing in negative pressure path 28c by attaching filter 82 to slit 20e. By this means, negative pressure means 20 can be prevented from failing to operate properly. In addition, evaporated materials 13 can be prevented from flowing in the lens 26g side.

(Embodiment 4)

Figure 15:
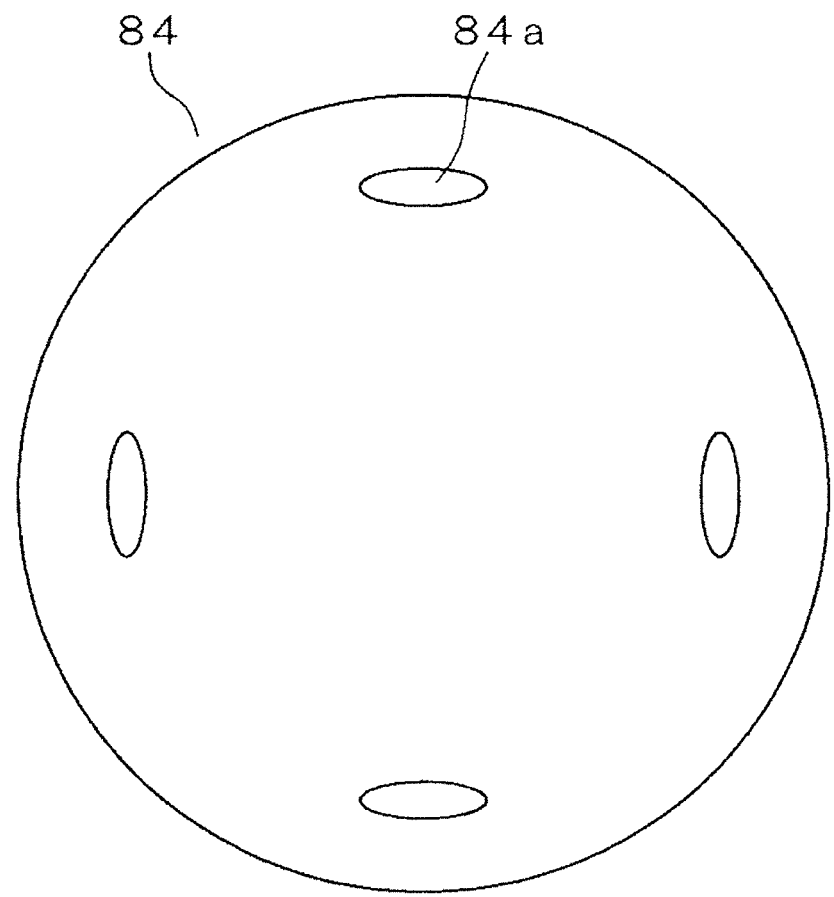
FIG. 15 is a plane view of the primary parts of the cover unit mounted to and removed from the sensor holding section of the blood test apparatus according to embodiment 4 of the present invention.
Figure 16:
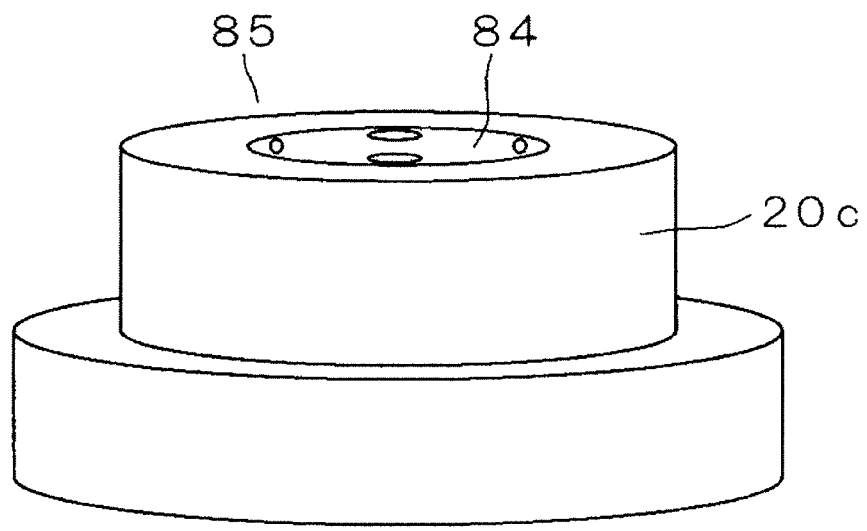
FIG. 16 is a perspective view of the cover unit mounted to and removed from the sensor holding section of the blood test apparatus according to embodiment 4.
Figure 17:
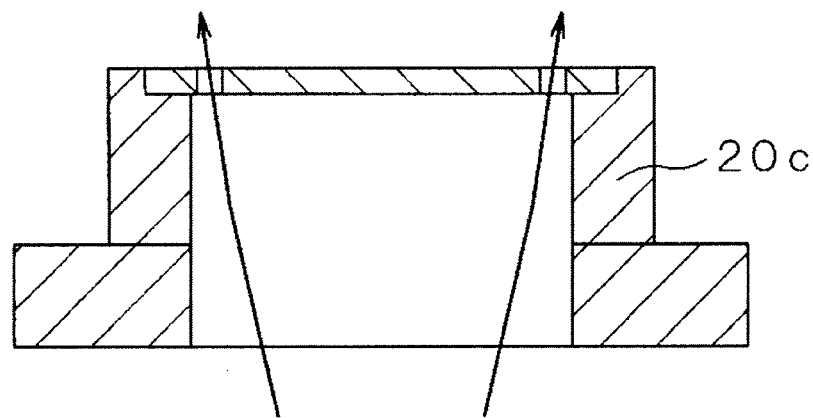
FIG. 17 is a cross sectional view of the cover unit mounted to and removed from the sensor holding section of the blood test apparatus according to embodiment 4.

FIG. 15 is a plane view of the main parts of a glass part, which is the cover member of the cover unit mounted to and removed from sensor holding section 25 of blood test apparatus according to embodiment 4; FIG. 16 is a perspective view of the cover unit; and FIG. 17 is a cross sectional view of the cover unit. The same components as in FIG. 4 and FIG. 5 will be assigned the same reference numerals and overlapping descriptions will be omitted.

As shown in FIG. 15 to FIG. 17, the cover unit in this embodiment uses cover glass 84 having negative pressure flowing hole 84a.

Cover glass 84 has negative pressure flowing hole 84a at a certain distance from the center of the optical axis of laser light from laser unit 26. Negative pressure flowing hole 84a may be formed in any positions other than the part where laser light 26h emitted from laser unit 26 passes through.

Slits 20e (see FIG. 4) are not required by providing negative pressure flowing hole 84a in cover glass 84. In addition, since these slits 20e are not required, it is not necessary to provide a gap between cylindrical member 20c and the wall surface of negative pressure chamber 28a.

(Embodiment 5)

Figure 18:
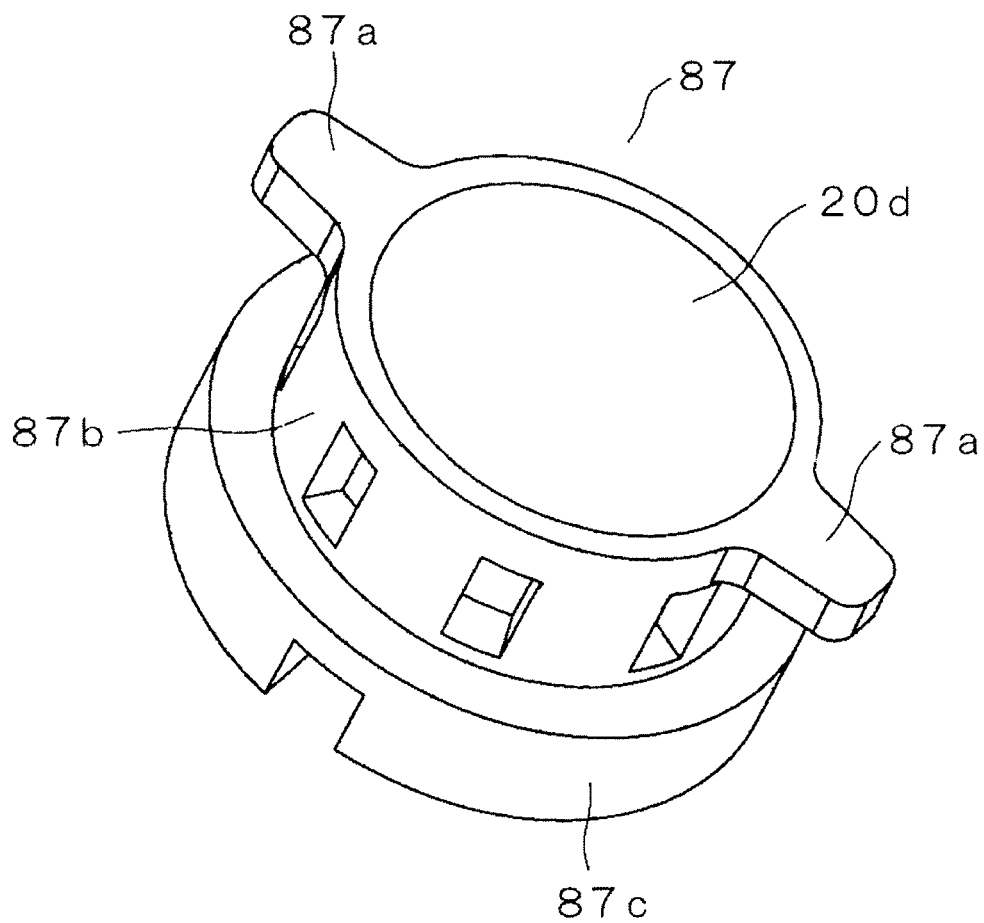
FIG. 18 is a perspective view of the cover unit mounted to and removed from the sensor holding section of the blood test apparatus according to embodiment 5 of the present invention.
Figure 19:
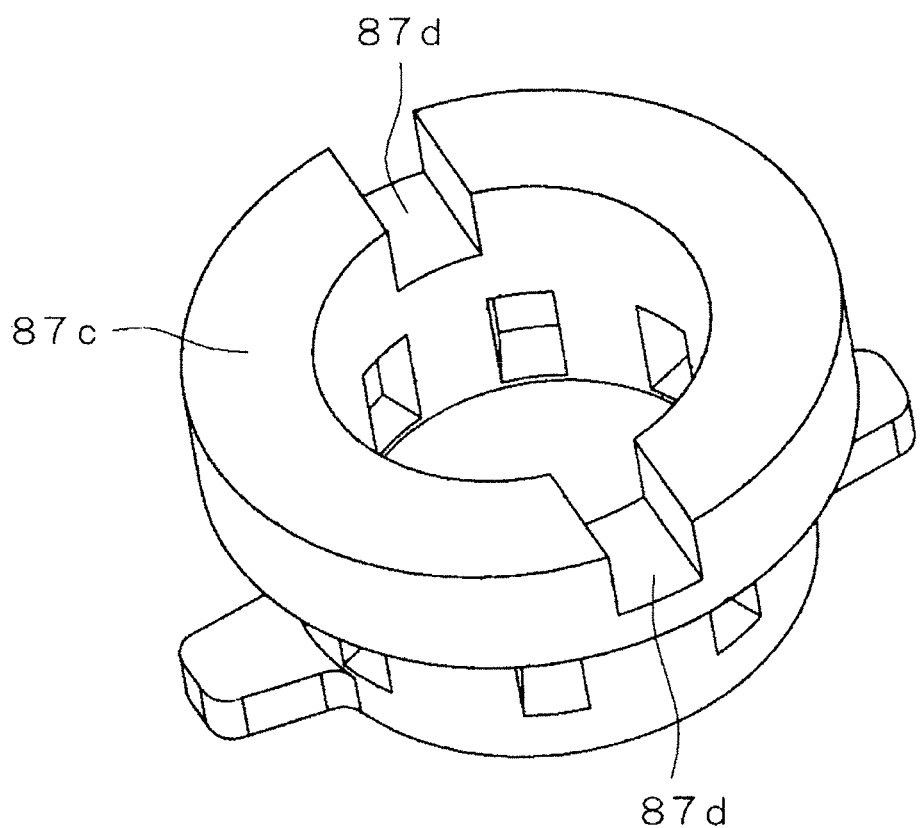
FIG. 19 is a perspective view from below of the cover unit mounted to and removed from the sensor holding section of the blood test apparatus according to embodiment 5.

FIG. 18 is a perspective view of the cover unit mounted to and removed from sensor holding section 25 of the blood test apparatus according to embodiment 5, and FIG. 19 is a perspective view of the cover unit from below. The same components as in FIG. 4 will be assigned the same reference numerals and overlapping descriptions will be omitted.

As shown in FIG. 18 and FIG. 19, cover unit 87 has two engaging pawls 87a provided in a straight line, on the upper surface of cylindrical member 87b. In addition, concave parts corresponding to pawls 87a are provided on the wall surface of negative pressure chamber 28a. Moreover, two grooves 87d are provided in a straight line in the lower part of flange 87c.

By this configuration, cover unit 87 is inserted in negative pressure chamber 28a, and a coin having a small diameter and so forth is fitted in grooves 87d and rotated in the positive direction, so that cover unit 87 is mounted in negative pressure chamber 28a through pawls 87a. In addition, when cover unit 87 is removed from negative chamber 28a, a coin having a small diameter is fitted in grooves 87d and rotated in the opposite direction, so that pawls 87a are removed from the concave parts of the wall surface of negative pressure chamber 28a and therefore cover unit 87 can be easily removed from negative pressure chamber 28a.

(Embodiment 6)

Figure 20:
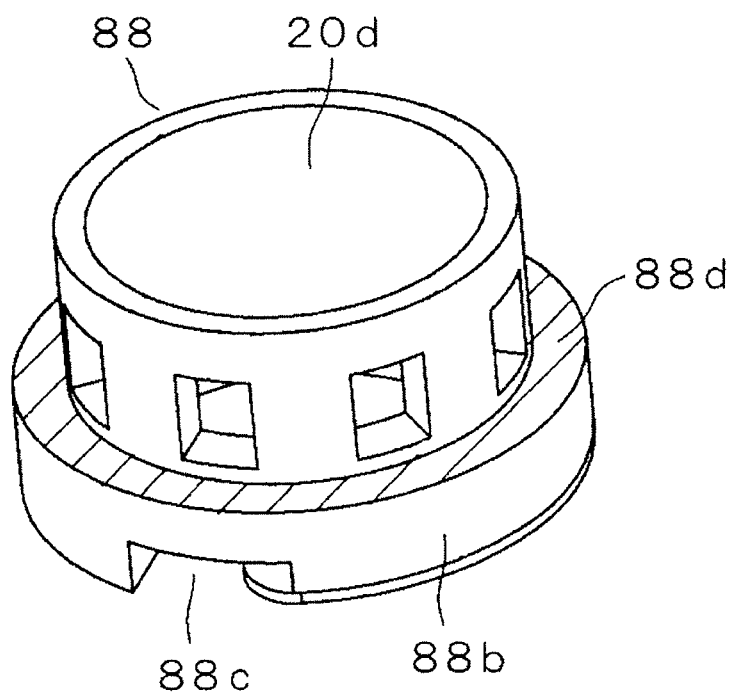
FIG. 20 is a perspective view of the cover unit mounted to and removed from the sensor holding section of the blood test apparatus according to embodiment 6 of the present invention.
Figure 21:
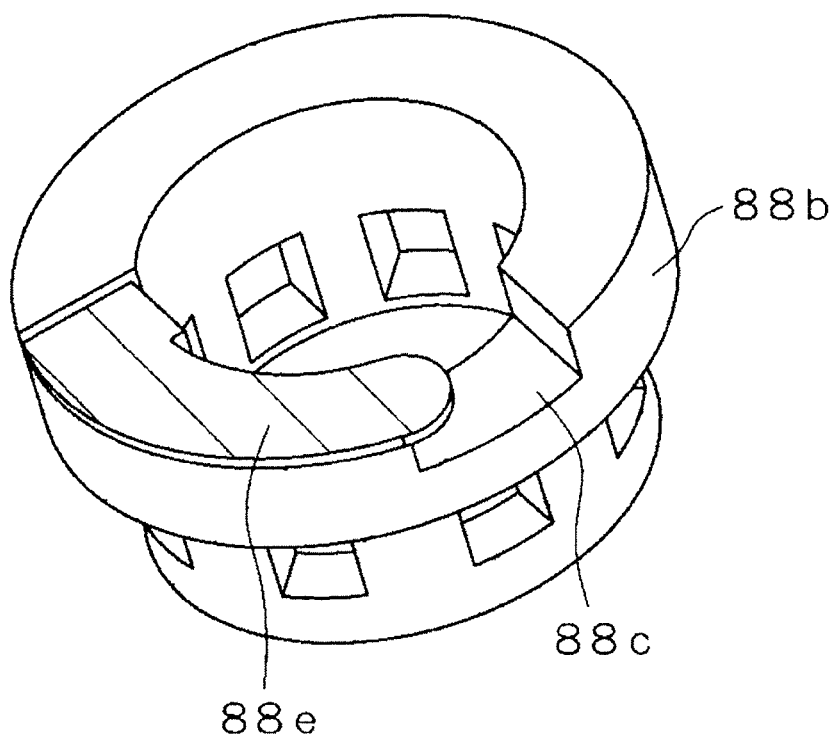
FIG. 21 is a perspective view from below of the cover unit mounted to and removed from the sensor holding section of the blood test apparatus according to embodiment 6 of the present invention.
Figure 22:
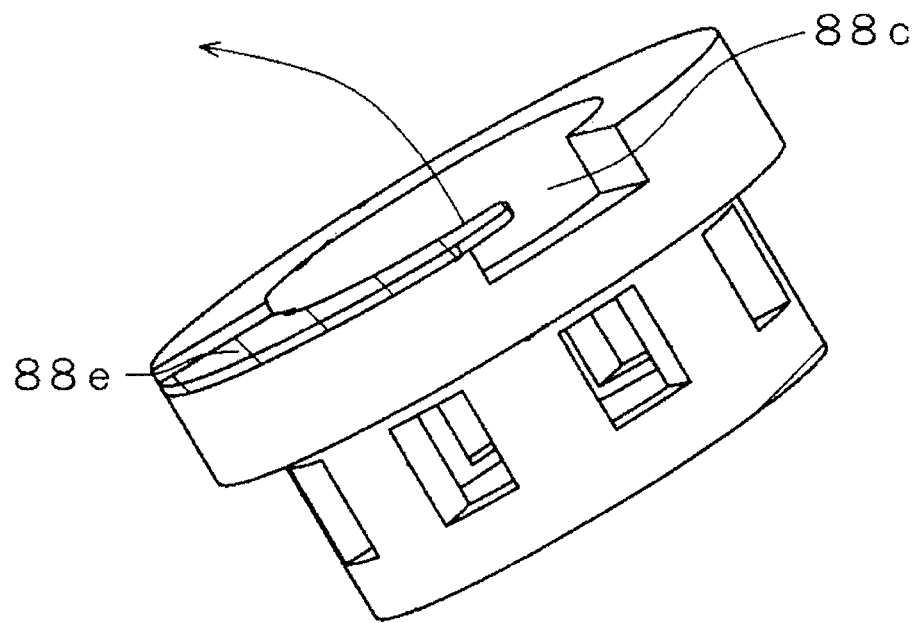
FIG. 22 is a perspective view from the side surface of the cover unit mounted to and removed from the sensor holding section of the blood test apparatus according to embodiment 6.

FIG. 20 is a perspective view of the cover unit mounted to and removed from sensor holding section 25 of the blood test apparatus according to embodiment 6 of the present invention; FIG. 21 is a perspective view of the cover unit from below; and FIG. 22 is a perspective view of the cover unit from the lateral side. The same components as in FIG. 4 will be assigned the same reference numerals and overlapping descriptions will be omitted.

As shown in FIG. 20 to FIG. 22, adhesive (locking tape) 88d is attached to the upper portion of flange 88b of cover unit 88.

In addition, the position in which the adhesive is provided is not limited. For example, the adhesive may be provided in a position corresponding to adhesive 88d in the negative pressure chamber 28a side. Cover unit 88 can be mounted to negative pressure chamber 28a by adhesive 88d.

As shown in FIG. 21, removing film 88e is provided on the bottom part of flange 88b and concave part 88c is provided in the position corresponding to the tip of film 88e. Cover unit 88 can be removed from negative chamber 28a by pulling this film 88e. In addition, since flange 88b has concave part 88c, film 88e can be easily grabbed.

(Embodiment 7)

Figure 23:
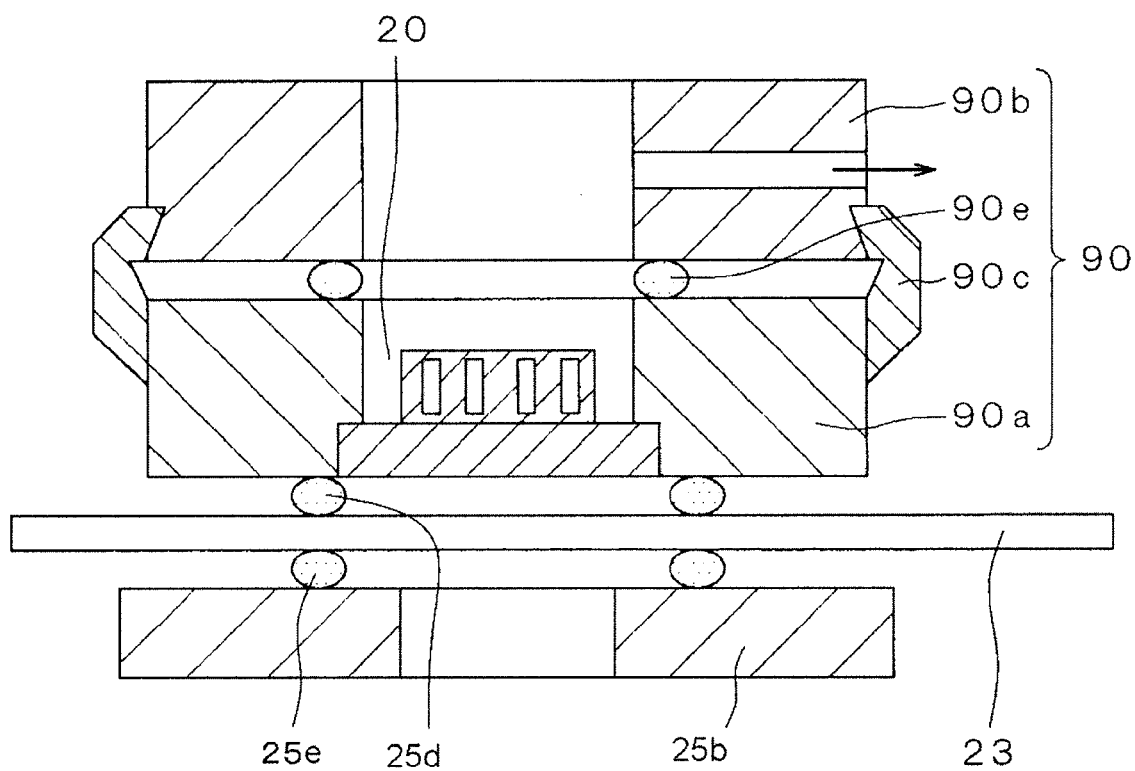
FIG. 23 is a cross sectional view of the neighborhood of the sensor holding section including the sensor of the blood test apparatus according to embodiment 7 of the present invention.

FIG. 23 is a cross sectional view showing the neighborhood of the puncturing section including the sensor of the blood test apparatus according to embodiment 7 of the present invention. The same components as in FIG. 3 will be assigned the same reference numerals and overlapping descriptions will be omitted.

As shown in FIG. 23, upper holder 90 is divided into two stages, which are holder 90a in which cover unit 20 is mounted and holder 90b in which cover unit 20 is not mounted, and two stages of holder 90 are removeably coupled with one another by coupling section 90c. Airtightness is improved by providing seal member 90e between these holder 90a and 90b.

According to the present embodiment, since holder 90a is lager than cover unit 20, holder 90a is easily mounted to and removed from cover unit 20. First, this holder 90a is removed, and then cover unit 20 can be mounted and removed. Therefore, cover unit 20 can be easily mounted and removed.

(Embodiment 8)

Figure 1:
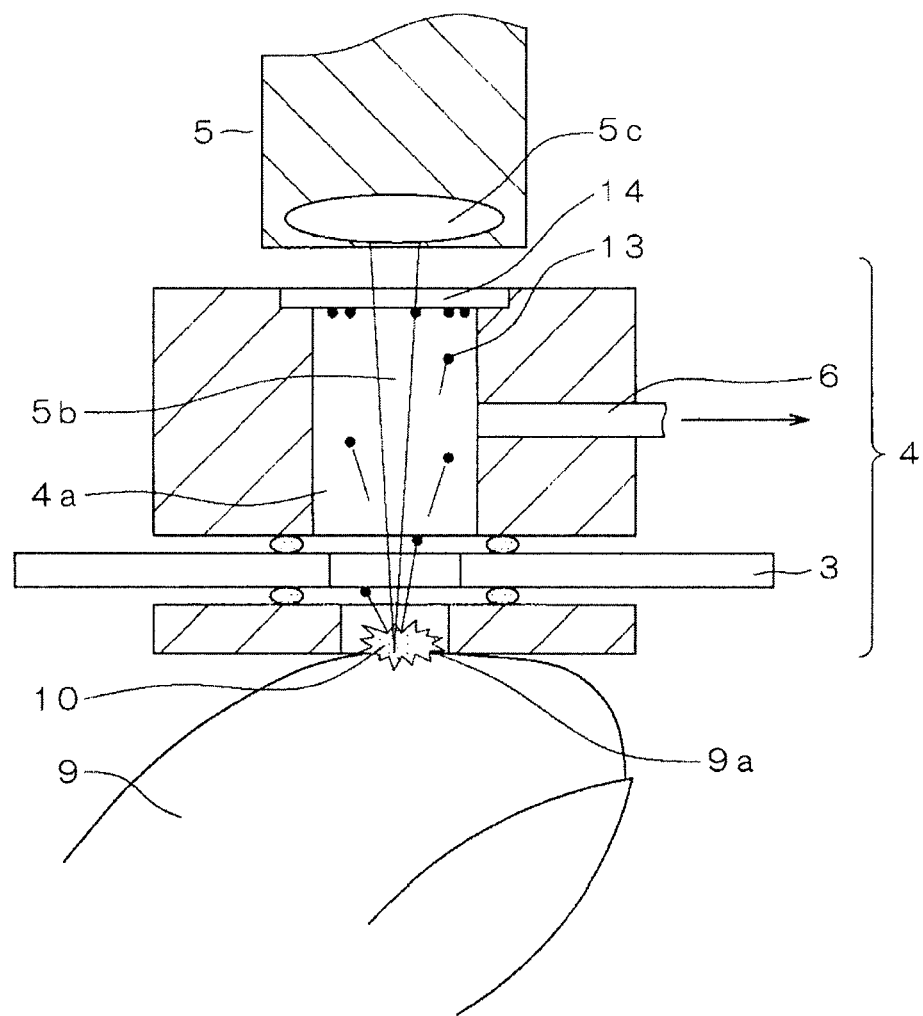
FIG. 1 is a cross sectional view of an enlarged puncturing section of a conventional blood test apparatus.

Conventionally, since the evaporated materials adhere on the lens and so forth in the laser path as a result of puncturing with laser, cover glass 14 protects the lens and so forth (see FIG. 1). If cover glass 14 is stained, laser light 5b is attenuated and therefore a planned puncturing depth cannot be obtained. As a result of this, necessary blood 10 enough to measure cannot be obtained. If sufficient blood 10 is not obtained, the blood test cannot be performed accurately. That is, the number of times puncturing is performed has been limited because evaporated materials adhere on cover glass 14. Moreover, when evaporated materials adhere too much, it has been necessary to replace the cover glass.

According to each of the above-described embodiments 1 to 7, blood test apparatus 21 has; housing 22; sensor holding section 25 provided in housing 22; laser unit 26 provided to face sensor holding section 25; negative pressure chamber 28a provided in sensor holding section 25; and cover unit 20 that is removably mounted to negative pressure chamber 28a and that prevents the evaporated materials from adhering on the laser emitting outlet of laser unit 26. Cover unit 20 has cover glass 20d provided on the optical axis of laser light from laser unit 26 and hole 20e that penetrates from the outside to the inside of cover unit 20. By this means, (1) cover glass 20 allows laser light 26h to pass through without attenuating laser light 26h; (2) it is possible to suck in sensor holding section 25; (3) it is possible to remove evaporated materials 13; and (4) it is possible to easily replace cover glass 20.

With embodiment 8, the configuration of the cover unit mounted to and removed from sensor holding section 25 will be described in detail.

FIG. 24A is a plane view schematically showing cover unit 120 mounted to and removed from sensor holding section 25 of the blood test apparatus according to embodiment 8 of the present invention, and FIG. 24B is a cross sectional view of the cover unit 120.

In FIG. 24A and FIG. 24B, cover unit 120 has a hat shape having annular flange 120a in its lower part and cylindrical part 120b, and cavity 120c is formed inside cover unit 120. Cover glass 120d is mounted on the upper portion of cover glass 120d. Cover glass 120d is made of glass allowing light to pass through (sapphire glass, fluorite and borosilicate glass), or made of fluorocarbon resin (PFA, FEP, PTFE and so forth).

A plurality of slits 120e connecting cavity 120c with the outside are formed in cylindrical member 120b and a negative pressure communicates negative pressure chamber 128a with cavity 120c through slits 120e.

Now, the material for cover glass 120d will be described.

As the material for a laser light transmission plate, material allowing light having the laser wavelength to pass through is preferable in order to attenuate the power of laser light as far as possible. If the wavelength of laser light is 2 to 3 μm, sapphire glass, synthetic quartz, fluorinated glass and so forth are preferable. In addition, if the thickness of the laser light transmission plate is about 0.1 mm to 0.3 mm, the transmissivity of 90% to 70% can be assured even if borosilicate glass is used.

When borosilicate glass is used, it absorbs heat a little and also absorbs an impulse wave, and therefore it is possible to damage a part through which laser light passes. In order to prevent such a problem, it is preferable that cover glass 120d is located in a position near the laser lens, that is, a position in which the energy density of laser light per unit area is small. Therefore, as shown in FIG. 24B, it is preferable that height H of cylindrical member 120b is higher. However, the distance between the lens of the laser and the punctured portion depends on the focal distance of the lens. Here, since the distance between the laser lens and the punctured portion is around 20 mm, height H is set to equal to or less than the focal distance.

FIG. 25 is a drawing explaining materials for the cover glass using a table.

As the material for cover glass 120d, it is necessary to consider heat resistance to overcome an amount of heat generated when laser light passes through, the strength to overcome the impulse wave generated when laser light passes through, and the material cost.

In FIG. 25, preferably, the material for the film preferably has a strength preventing the film from breaking due to the absorption when laser light passes through, and a fluoride film is preferable as the material when the laser has a wavelength of 3 μm.

Moreover, when a fluoride film is used as the material, the film is disposed apart from the focal position, so that the film does not break. In addition, when a fluoride film is used, the cost can be reduced.

Glass may be used as the material for cover glass 120d. Although glass has good heat resistance and strength, the transmittivity is reduced unless its thickness is equal to or less than 0.1 mm. When the thickness is reduced, the strength is degraded and micro crack occurs in the portion where laser light passes through by the impulse wave when laser light passes through. In order to solve this problem, the glass is disposed in a position apart from the focal position and therefore the strength is assured. Although the cost of glass is higher than that of film, when glass is used as the material, the running cost is reduced because the glass can be removed and washed. Since film and glass both have their drawback and advantage, preferably, film and glass are selectively used such that film is used as a replaceable material and glass is used as a repeatedly used material to be used more than once and washed.

Figure 26:
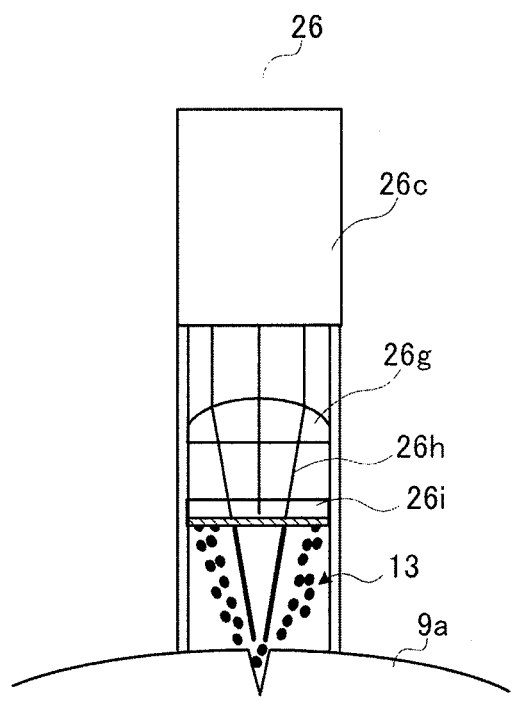
FIG. 26 is a drawing showing the scattering of evaporated materials during the puncturing operation with laser light in the blood test apparatus according to embodiment 8.
Figure 27:
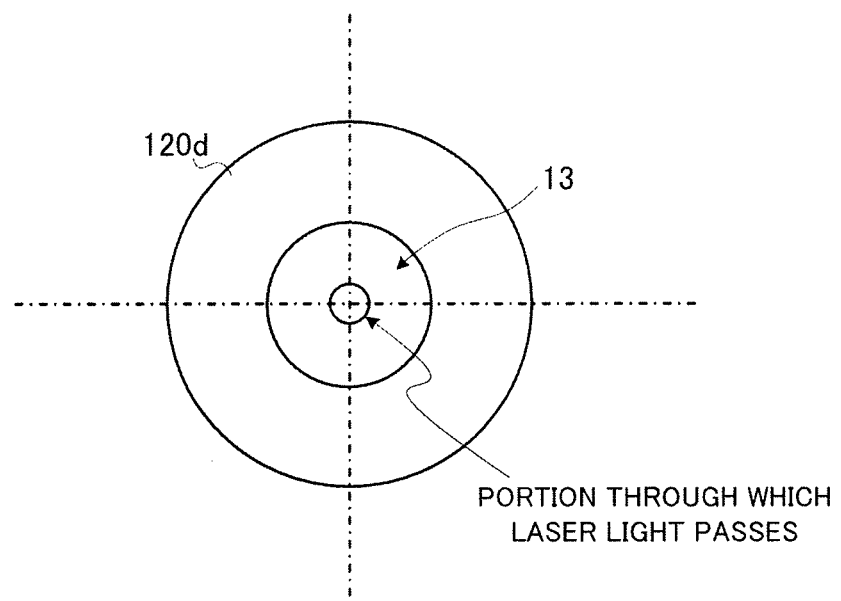
FIG. 27 is a drawing explaining the adhering condition of the evaporated materials on the cover glass of the blood test apparatus according to embodiment 8.

FIG. 26 is a drawing showing the scattering of the evaporated materials during a puncturing operation and FIG. 27 is a drawing explaining an adhering condition of evaporated materials on cover glass 120d. The same components as in FIG. 10 will be assigned the same reference numerals and overlapping descriptions will be omitted.

In FIG. 26, laser light 26h is emitted from laser rod 26c of laser unit 26. The light path of emitted laser light 26h is narrowed down by convex lens 26g and focused near skin 9a of the patient. Laser light 26h punctures skin 9a, and when skin 9a is punctured, firstly evaporated materials 13 scatter. These evaporated materials 13 adhere on laser light transmission plate 26i. Here, with the present embodiment, cover unit 120 is mounted to sensor holding section 25 of the blood test apparatus in order to prevent evaporated materials 13 from adhering on laser light transmission plate 26i. Cover glass 120d of cover unit 120 prevents evaporated materials 13 from adhering on laser light transmission plate 26i. Since FIG. 26 is a drawing to explain the scattering of evaporated materials, cover unit 120 is omitted in the figure.

According to the evaluation test performed by the inventors, the fact was found that evaporated materials 13 are evaporated toward a position other than the light path of laser light when the puncturing operation with laser light is performed. When the diameter over which skin 9a is punctured is 0.3 mm and cover glass 120d is located just above skin 9a, evaporated materials 13 adhere on the area other than the punctured area of 0.3 mm. Therefore, when height H of cylindrical member 120b shown in FIG. 24B is higher, evaporated materials 13 adhere over a wider area.

In the present embodiment, the exit area of laser light has a rod diameter of 2 mm. According to this evaluation test, evaporated materials 13 adhere on the outside of the area having a diameter equal to or more than Φ2 mm.

The adhering condition of evaporated materials 13 on cover glass 120d is shown in FIG. 27. As shown in FIG. 27, the area where laser light passes through has a diameter from 0.3 mm up to 2 mm. The diameter of cover glass 120d is 5 mm to 10 mm.

Next, the conditions of the holder part and the suction path will be described.

Figure 28A:
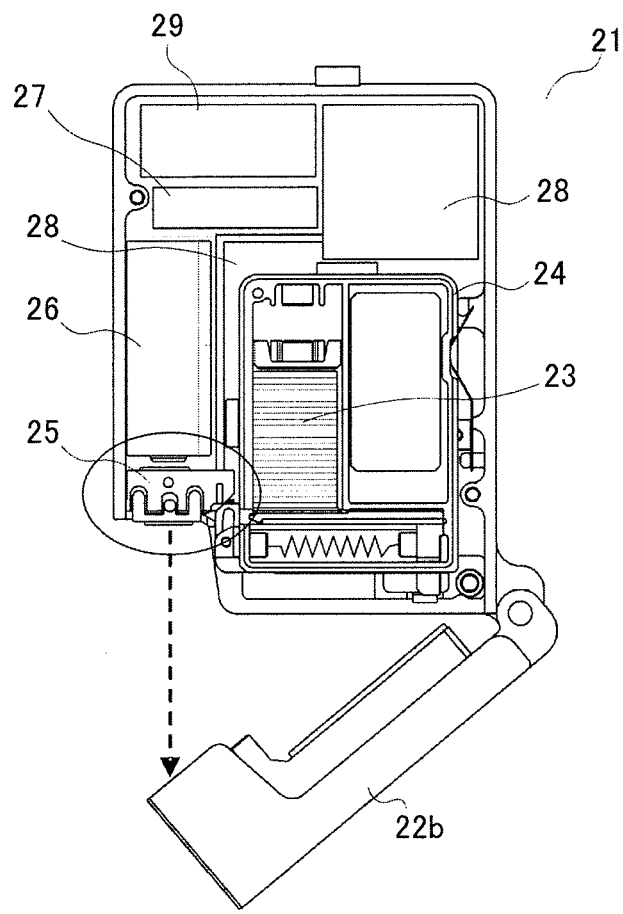
FIG. 28A is a perspective layout drawing of the blood test apparatus according to embodiment 8.
Figure 28B:
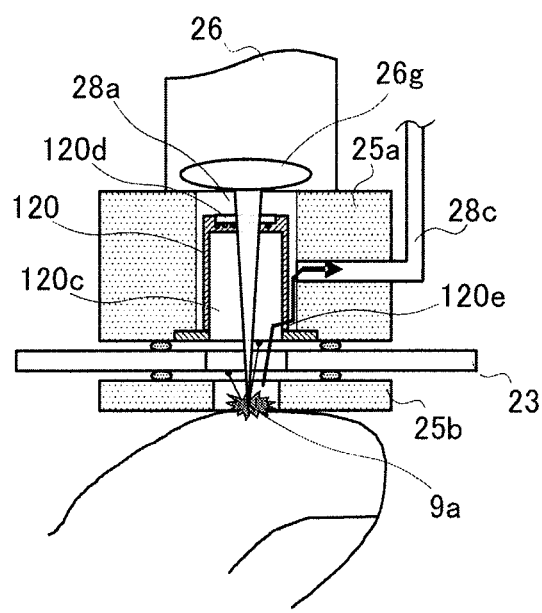
FIG. 28B is a cross sectional view of the sensor holding section and its neighborhood in the blood test apparatus according to embodiment 8.

FIG. 28A is a perspective layout drawing of the blood test apparatus according to embodiment 8, and FIG. 28B is a cross sectional view of sensor holding section 25 and its neighborhood in the blood test apparatus. The same components as in FIG. 2 and FIG. 3 will be assigned the same reference numerals and overlapping descriptions will be omitted.

In FIG. 28B, sensor holding section 25 is composed of upper holder 25a and lower holder 25b, and negative pressure chamber 28a through which laser light penetrates is formed in upper holder 25a. In addition, negative pressure path 28c connecting negative pressure means 28, which serves as a suction path, is provided on the side wall surface of negative pressure chamber 28a. Moreover, cover unit 120 is removably mounted to cover unit 120 below negative pressure chamber 28a.

Cover glass 120d is mounted on the upper part of cylindrical member 120b of cover unit 120. Therefore, the distance between the laser lens and the cover glass 120d is determined based on height H of cylindrical member 120b. As described above, height H of cylindrical member 120b differs depending on the material for cover glass 120d. Considering a case in which film is used as the material, preferably, height H of cylindrical member 120b is higher. However, evaporated materials 13 adhere on the wide area inside cylindrical member 120b.

That is, when skin 9a is punctured, evaporated materials 13, which evaporate from the punctured location toward the convex lens 26g side of laser unit 26, diffuse with a predetermined spread from the laser light axis. Such a spread of evaporated materials 13 differs depending on the conditions. Height H of cylindrical member 120b is one of the conditions.

In the present embodiment, cover unit 120 is formed to have a derby hat shape approximately occupying the inside of negative pressure chamber 28a as shown in FIG. 28B. On the other hand, in order to assure a negative pressure in negative chamber 28a and storing section 34 (see FIG. 3), an appropriate gap is formed between the outer circumference of cylindrical member 120b and the inner circumference of negative pressure chamber 28a, and a plurality of slits 120e that couple cavity 120c with the outside are formed on the lower part of cylindrical member 120b. As shown by the arrow in FIG. 28B, a negative pressure in storing section 34 and cavity 120c is in communication with negative pressure chamber 28a and negative pressure path 28c through this slits 120e.

As described above, cover unit 120 is characterized in that: height H of cylindrical member 120b is set; and slits 120e are formed on the lower part of cylindrical member 120b, that is, in positions near sensor holding section 25. Cover unit 120 has slits 120e disposed on the lower part of cylindrical member 120b near sensor holding section 25 and therefore assures a sufficient negative pressure and prevents evaporated materials 13 from scattering toward cover glass 120d as much as possible. By this means, the number of times to wash cover glass is reduced.

The above description is illustration of the preferred embodiments of the present invention and the scope of the invention is not limited to this.

Moreover, although the names "blood test apparatus" is used in the present embodiment for convenience of explanation, it goes without saying that the name of the apparatus may be a "blood analysis apparatus", a "puncturing apparatus", a "body fluid measurement apparatus" and so forth.

Moreover, for each component constituting the above-described blood test apparatus, such as the kind of cartridge, the number and the connection method thereof are not limited.

The disclosure of Japanese Patent Application No. 2007-228532, filed on Sep. 4, 2007, including the specification, drawings and abstract, is incorporated herein by reference in its entirety.

INDUSTRIAL APPLICABILITY

The present invention is applicable to a blood test apparatus that punctures skin by a puncturing means such as a laser emitting device, samples blood exuding from the skin and analyzes the components of the blood. Since the blood test apparatus has the radiant intensity independent of the number of times puncturing is performed, it is suitable for a blood test apparatus using a laser unit.

The invention claimed is:

1. A blood test apparatus comprising:
   a housing;
   a laser emitting device that is provided in the housing such that the laser emitting device does not contact skin to be punctured, that punctures skin with laser light, and that has a convex lens;
   a blood sensor that analyzes blood exuding from the punctured skin;
   a holder that holds the blood sensor;
   a negative pressure chamber that is provided in the holder and through which the laser light from the laser emitting device penetrates;
   a negative pressure creater that creates a negative pressure in a negative pressure space hermetically sealed between the skin and the negative pressure chamber; and
   a cover that is removably mounted to the negative pressure chamber, that is removable independently of the blood sensor and that is disposed at a position closer to the laser emitting device than is the blood sensor,
   wherein the cover includes:
   a cylindrical member that surrounds an optical axis of a laser light from the laser emitting device;
   a cover member that is disposed at an end of the cylindrical member facing the laser emitting device, that extends traverse to the path of the laser light and that is positioned so that the laser light passes through the cover member; and
   a communication path that communicates between an inside of the cylindrical member and the negative pressure chamber.

2. The blood test apparatus according to claim 1, wherein the cylindrical member is arranged such that there is gap between the cylindrical member and a wall surface of the negative pressure chamber of the holder.

3. The blood test apparatus according to claim 1, wherein the communication path is a slit provided in the cylindrical member.

4. The blood test apparatus according to claim 1, wherein the cover member comprises glass.

5. The blood test apparatus according to claim 1, wherein the communication path has a filter.

6. The blood test apparatus according to claim 1, wherein the communication path is positioned at a predetermined distance from the optical axis of the laser light from the laser emitting device.

7. The blood test apparatus according to claim 1, wherein the cylindrical member is a circular cylinder and is provided with a pawl that engages with a bottom part of the holder.

8. The blood test apparatus according to claim 1, wherein the cylindrical member is a circular cylinder and is composed of a first cylindrical member that is provided with a pawl engaging with a bottom part of the holder and a second cylindrical member that is mounted in the first cylindrical member and that is provided with the communication path.

9. The blood test apparatus according to claim 1, wherein:
   the holder is composed of an upper holder and a lower holder that contacts the skin;
   the cylindrical member is a circular cylinder; and
   the cylindrical member has a bottom part having a flange structure and an adhesive part that attaches the bottom part to a bottom surface of the upper holder.

10. The blood test apparatus according to claim 1, wherein the holder is composed of a plurality of stages that can be separated in the direction of the optical axis of the laser light from the laser emitting device.

11. The blood test apparatus according to claim 1, wherein:
the cylindrical member is a circular cylinder and has a bottom part having a flange structure; and
a height from a bottom surface of the bottom part to the cover member is shorter than a focal distance of the convex lens.

12. The blood test apparatus according to claim 1, wherein the cover prevents blood exuding from the punctured skin from staining the convex lens.

13. The blood test apparatus according to claim 1, wherein the cover member is configured such that evaporated material from the punctured skin is adhered to the cover member.

14. The blood test apparatus according to claim 1, wherein the cover member is arranged between the blood sensor and the laser emitting device.

15. The blood test apparatus according to claim 1, wherein the cylindrical member and the cover member are unitarily removable.

16. The blood test apparatus according to claim 1, wherein the communication path comprises a plurality of circumferentially spaced slits in the cylindrical member.

17. The blood test apparatus according to claim 5, said filter comprising a membrane that permits passage of air and that precludes passage of solid particles.

18. The blood test apparatus according to claim 1, said blood sensor being positioned beneath said cover.

19. The blood test apparatus according to claim 1, said cover member being spaced from said blood sensor by a length of said cylindrical member.

20. The blood test apparatus according to claim 1, wherein the communication path includes at least one aperture provided in the cover member.

* * * * *